United States Patent [19]
Martin et al.

[11] Patent Number: 5,213,804
[45] Date of Patent: * May 25, 1993

[54] SOLID TUMOR TREATMENT METHOD AND COMPOSITION

[75] Inventors: Francis J. Martin, San Francisco; Martin C. Woodle, Menlo Park; Carl Redemann, Walnut Creek; Annie Yau-Young, Palo Alto, all of Calif.

[73] Assignee: Liposome Technology, Inc., Menlo Park, Calif.

[*] Notice: The portion of the term of this patent subsequent to May 7, 2008 has been disclaimed.

[21] Appl. No.: 642,321

[22] Filed: Jan. 15, 1991

Related U.S. Application Data

[63] Continuation-in-part of Ser. No. 425,224, Oct. 20, 1989, Pat. No. 5,013,556.

[51] Int. Cl.$^5$ .................... A61K 9/127; A61K 31/765
[52] U.S. Cl. .................... 424/450; 424/426; 424/78.31
[58] Field of Search .................... 424/450; 260/403; 428/402.2; 264/4, 4.1

[56] References Cited

U.S. PATENT DOCUMENTS

| | | | |
|---|---|---|---|
| 3,993,754 | 11/1976 | Rahman et al. | 424/177 |
| 4,426,330 | 1/1984 | Sears | 260/403 |
| 4,501,728 | 2/1985 | Geho et al. | 424/450 |
| 4,534,899 | 8/1985 | Sears | 260/403 |
| 4,769,250 | 9/1988 | Forssen | 424/450 |
| 4,797,285 | 1/1989 | Barenholz et al. | 424/450 |
| 4,837,028 | 6/1989 | Allen et al. | 424/450 |
| 4,863,739 | 9/1989 | Perez-Solar et al. | 424/450 |
| 4,885,172 | 12/1989 | Bally et al. | 424/450 |
| 4,904,479 | 2/1990 | Illum | 424/490 |
| 4,917,893 | 4/1990 | Okada et al. | 424/423 |
| 4,920,016 | 4/1990 | Allen et al. | 424/450 |
| 5,013,556 | 5/1991 | Woodle et al. | 424/450 |

FOREIGN PATENT DOCUMENTS

| | | |
|---|---|---|
| 82303789 | 2/1983 | European Pat. Off. |
| 84301510 | 9/1984 | European Pat. Off. |
| 89402290 | 2/1990 | European Pat. Off. |
| 1-249798 | 10/1989 | Japan |
| 63-76862 | 12/1989 | Japan |
| WO88/04924 | 7/1988 | PCT Int'l Appl. |
| WO90/04384 | 5/1990 | PCT Int'l Appl. |
| 2185397A | 7/1987 | United Kingdom |

OTHER PUBLICATIONS

Illum, L., et al., Life Sciences, 44:1553 (1987).
Illum, L., et al., J. Pharm. Sci., 72(9):1086 (1983).
Illum, L., et al., Life Sciences, 40:367 (1987).
Illum, L., et al., FEBS 167(1):79 (1984).
Weinstein, J. N., et al., Liposomes from Biophysics to Therapeutics, ed. M. J. Ostro, pp. 277-388 (1987).
Pozanansky, M. J., et al., Pharm. Rev. 36(4):277 (1984).
Poste, G., et al. Targeted Drug Delivery and Biological Interaction, ed. G. Grejoriadis, CRC Press, pp. 1-28 (1984).
Weinstein, J. N., et al., Pharmac. Ther. 24:207 (1984).
Tomlinson, E., DN&P 2(1):5 (1989).

Primary Examiner—Thurman K. Page
Attorney, Agent, or Firm—Peter J. Dehlinger

[57] ABSTRACT

A liposome composition for localizing an anti-tumor compound to a solid tumor via the bloodstream. The liposomes, which contain the agent in entrapped form, are composed of vesicle-forming lipids and between 1-20 mole percent of a vesicle-forming lipid derivatized with hydrophilic biocompatible polymer, and have sizes in a selected size range between 0.07 and 0.12 microns. After intravenous administration, the liposomes are taken up by the tumor within 24-48 hours, for site-specific release of entrapped compound into the tumor. In one composition for use in treating a solid tumor, the compound is an anthracycline antibiotic drug which is entrapped in the liposomes at a concentration of greater than about 50 μg agent/μmole liposome lipid. The method results in regression of solid colon and breast carcinomas which are refractory to anthracycline antibiotic drugs administered in free form or entrapped in conventional liposomes.

15 Claims, 18 Drawing Sheets

X=CH$_3$ for lactic acid polymers
or H for glycolic acid polymers n=10-50

SOLID TUMOR TREATMENT METHOD AND COMPOSITION

This application is a continuation-in-part of copending application Ser. No. 425,224, filed Oct. 20, 1989 issued May 7, 1991 as U.S. Pat. No. 5,013,556.

FIELD OF THE INVENTION

The present invention relates to a liposome composition and method, particularly for use in tumor diagnostics and/or therapeutics.

REFERENCES

Allen, T. M., (1981) Biochem. Biophys, Acta 640. 385397. Allen, T. M., and Everest, J. (1983) J. Pharmacol. Exp. Therap. 226. 539-544.

Altura, B. M. (1980) Adv. Microcirc. 9, 252-294.

Alving, C. R. (1984) Biochem. soc. Trans. 12. 342344.

Ashwell, G., and Morell, A. G. (1974) Adv. Enzymology 41, 99-128.

Czop, J. K. (1978) Proc. Natl. Acad. Sci. U.S.A 75:3831.

Durocher, J. P., et al. (1975) Blood 45:11.

ellens, H., et al. (1981) Biochim. Biophys. Acta 674. 10-18.

Gabizon, A., Goren, D. and Barenholz, Y. (1988) Israel J. Med. Sci. 24, 512-517.

Gabizon, A., Huberty, J., Straubinger, R. M., Price, D. C. and Papahadjopoulos, D. (1988-1989) J. Liposome Resh. 1, 123-135.

Gabizon, A., Shiota, R. and Papahadjopoulos, D. (1989) J. Natl. Cancer Inst. 81, 1484-1488.

Gregoriadis, G., and Ryman, B.E. (1972) Eur. J. Biochem. 24, 485-491.

Gregoriadis, G., and Neerunjun, D. (1974) Eur. J. Biochem. 47, 179-185.

Gregoriadis, G., and Senior, J. (1980) FEBS Lett. 119, 43-46.

Greenberg, J. P., et al (1979) Blood 53:916.

Hakomori, S. (1981) Ann. Rev. Biochem. 50, 733-764.

Hong, K., Friend, D., Glabe, C. and Papahadjopoulos (1984) Biochem. Biophys. Acta 732,320-323.

Hwang, K. J., et al. (1980) Proc. Natl. Acad. Sci. U.S.A. 77:4030.

Jain, K. J. (1989) J. Natl. Can. Inst. 81, 570-576.

Jonah, M. M., et al. (1975) Biochem. Biophys. Acta 401, 336-348.

Juliano, R. L., and Stamp, D. (1975) Biochem. Biophys. Res. Commun. 63. 651-658.

Karlsson, K. A. (1982) In: Biological Membranes, Vol. 4, D. Chapman (ed.) Academic Press, N.Y., pp. 1-74.

Kimelberg, H. K., et al. (1976) Cancer Res. 36,2949-2957.

Kirby, C. J. and Gregoriadis (1984) In: Liposome Technology, Vol. 3, G. Gregoriadis (ed.) CRC Press, Boca Raton, FL, p. 19.

Lee, K. C., et al., J. Immunology 125:86 (1980).

Lopez-Berestein, G., et al. (1984) Cancer Res. 44, 375-378.

Martin, F. J. (1990) In: Specialized Drug Delivery Systems—Manufacturing and Production Technology, P. Tyle (ed.) Marcel Dekker, N.Y., pp. 267-316.

Okada, N. (1982) Nature 299:261.

Poste, G., et al., in "Liposome Technology" Volume 3, page 1 (Gregoriadis, G., et al, eds.), CRC Press, Boca Raton (1984);

Poznansky, M. J., and Juliano, R. L. (1984) Pharmacol. Rev. 36. 277-336.

Richardson, V.J., et al. (1979) Br. J. Cancer 40, 3543.

Saba, T. M. (1970) Arch. Intern. Med. 126. 1031-1052.

Schaver, R. (1982) Adv. Carbohydrate Chem. Biochem. 40:131.

Scherphof, T., et al. (1978) Biochim.Biophys. Acta 542, 296-307.

Senior, J., and Gregoriadis, G. (1982) FEBS Lett. 145, 109-114.

Senior, J., et al. (1985) Biochim. Biophys. Acta 839, 1-8.

Storm, G., Roerdintz, Steerenberg, P. A. de Jong, W. H. and Crommelin, D. J. A. (1987) Can. Res. 47, 3366-3372.

Szoka, F., Jr., et al. (1978) Proc. Natl. Acad. Sci. U.S.A. 75:4194.

Szoka, F., Jr., et al. (1980) Ann. Rev. Biophys. Bioeng. 9:467.

Tice, T. R., et al., (1984) Pharmaceutical Technology, Nov. 1984, pp. 26-35.

Weinstein, J. W., et al., Pharmac Ther, 24:207 (1984).

Weise, D. L., et al., in Drug Carriers in Biology and Medicine, G. Gregoriadis, Ed.—Academic Press, N.Y., 1979, pp. 237-270.

Woodruff, J. J., et al. (1969) J. Exp. Med. 129:551.

BACKGROUND OF THE INVENTION

It would be desirable, for extravascular tumor diagnosis and therapy, to target an imaging or therapeutic compound selectively to the tumor via the bloodstream. In diagnostics, such targeting could be used to provide a greater concentration of an imaging agent at the tumor site, as well as reduced background level of the agent in other parts of the body. Site-specific targeting would be useful in therapeutic treatment of tumors, to reduce toxic side effects and to increase the drug dose which can safely be delivered to a tumor site.

Liposomes have been proposed as a drug carrier for intravenously (IV) administered compounds, including both imaging and therapeutic compounds. However, the use of liposomes for site-specific targeting via the bloodstream has been severely restricted by the rapid clearance of liposomes by cells of the reticuloendothelial system (RES). Typically, the RES will remove 80-95% of a dose of IV injected liposomes within one hour, effectively out-competing the selected target site for uptake of the liposomes.

A variety of factors which influence the rate of RES uptake of liposomes have been reported (e.g., Gregoriadis, 1974; Jonah; Gregoriadis, 1972; Juliano; Allen, 1983; Kimelberg, 1976; Richardson; Lopez-Berestein; Allen, 1981; Scherphof; Gregoriadis, 1980; Hwang; Patel, 1983; Senior, 1985; Allen, 1983; Ellens; Senior, 1982; Hwang; Ashwell; Hakomori; Karlsson; Schauer; Durocher; Greenberg; Woodruff; Czop; and Okada). Briefly, liposome size, charge, degree of lipid saturation, and surface moieties have all been implicated in liposome clearance by the RES. However, no single factor identified to date has been effective to provide long blood halflife, and more particularly, a relatively high percentage of liposomes in the bloodstream 24 hours after injection.

In addition to a long blood halflife, effective drug delivery to a tumor site would also require that the liposomes be capable of penetrating the continuous endothelial cell layer and underlying basement membrane surrounding the vessels supplying blood to a tumor. Although tumors may present a damaged, leaky endothelium, it has generally been recognized that for liposomes to reach tumor cells in effective amounts, the liposomes would have to possess mechanisms which facilitate their passage through the endothelial cell barriers and adjacent basement membranes, particularly in view of the irregular and often low blood flow to tumors and hence limited exposure to circulating liposomes (Weinstein). Higher than normal interstitial pressures found within most tumors would also tend to reduce the opportunity for extravasation of liposomes by creating an outward transvascular movement of fluid from the tumor (Jain). As has been pointed out, it would be unlikely to design a liposome which would overcome these barriers to extravasation in tumors and, at the same time, evade RES recognition and uptake (Poznansky).

In fact, studies reported to date indicate that even where the permeability of blood vessels increases, extravasation of conventional liposomes through the vessels does not increase significantly (Poste). Based on these findings, it was concluded that although extravasation of liposomes from capillaries compromised by disease may be occurring on a limited scale below detection levels, its therapeutic potential would be minimal (Poste).

SUMMARY OF THE INVENTION

One general object of the invention is to provide a liposome composition and method which is effective for tumor targeting, for localizing an imaging or anti-tumor agent selectively at therapeutic dose levels in systemic, extravascular tumors.

The invention includes, in one aspect, a liposome composition for use in localizing a compound in a solid tumor, as defined in Section IV below, via the bloodstream comprising: The liposomes forming the composition (i) are composed of vesicle-forming lipids, and between 1-20 mole percent of an vesicle-forming lipid derivatized with a hydrophilic polymer, and (ii) have an average size in a selected size range between about 0.07-0.12 microns. The compound is contained in the liposomes in entrapped form (i.e., associated with the liposome membrane or encapsulated within the internal aqueous compartment of the liposome).

In a preferred embodiment, the hydrophilic polymer is polyethyleneglycol, polylactic, polyglycolic acid or a polylactic-polyglycolic acid copolymer having a molecular weight between about 1,000-5,000 daltons, and is derivatized to a phospholipid.

For use in tumor treatment, the compound in one embodiment is an anthracycline antibiotic or plant alkaloid, at least about 80% of the compound is in liposome-entrapped form, and the drug is present in the liposomes at a concentration of at least about 20 μg and preferably above 50 μg compound/μmole liposome lipid in the case of the anthracycline antibiotics and 1 μg/μmole lipid in the case of the plant alkaloids.

In a related aspect, the invention includes a composition of liposomes characterized by:

(a) liposomes composed of vesicle-forming lipids and between 1-20 mole percent of a vesicle-forming lipid derivatized with a hydrophilic polymer, (b) a blood lifetime, as measured by the percent of a liposomal marker present in the blood 24 hours after IV administration which is several times greater than that of liposomes in the absence of the derivatized lipids;

(c) an average liposome size in a selected size range between about 0.07-0.12 microns, and (d) the compound in liposome-entrapped form.

Also disclosed is a method of preparing an agent for localization in a solid tumor, when the agent is administered by IV injection. In this case, following IV administration, the agent is carried through the bloodstream in liposome-entrapped form with little leakage of the drug during the first 48 hours post injection. By virtue of the low rate of RES uptake during this period, the liposomes have the opportunity to distribute to and enter the tumor. Once within the interstitial spaces of the tumor, it is not necessary that the tumor cells actually internalize the liposomes. The entrapped agent is released from the liposome in close proximity to the tumor cells over a period of days to weeks and is free to further penetrate into the tumor mass (by a process of diffusion) and enter tumor cells directly—exerting its anti-proliferative activity. The method includes entrapping the agent in liposomes of the type characterized above. One liposome composition preferred for transporting anthracycline antibiotic or plant alkaloid antitumor agents to systemic solid tumors would contain high phase transition phospholipids and cholesterol as this type of liposome does not tend to release these drugs while circulating through the bloodstream during the first 24-48 hours following administration.

In another aspect, the invention includes a method for localizing a compound in a solid tumor in a subject. The method includes preparing a composition of liposomes (i) composed of vesicle-forming lipids and between 1-20 mole percent of an vesicle-forming lipid derivatized with a hydrophilic polymer, (ii) having an average size in a selected size range between about 0.07-0.12 microns, and (iii) containing the compound in liposome-entrapped form. The composition is injected IV in the subject in an amount sufficient to localize a therapeutically effective dose of the agent in the solid tumor.

Also disclosed is a system for providing effective anti-tumor therapy for agents which possess intrinsic anti-tumor activity in vitro but, due to unfavorable biodistribution, toxicity and metabolism in vivo, do reach tumors in effective amounts by prior art methods of drug administration.

These and other objects and features of the present invention will become more fully apparent when the following detailed description of the invention is read in conjunction with the accompanying drawings.

DETAILED DESCRIPTION OF THE INVENTION

I. Preparation of Derivatized Lipids

Figure 1:
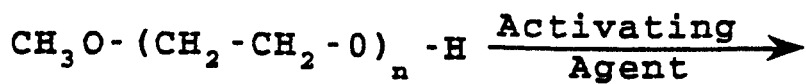
FIG. 1 illustrates a general reaction scheme for derivatizing a vesicle-forming lipid amine with a polyalkylether.
Figure 1:
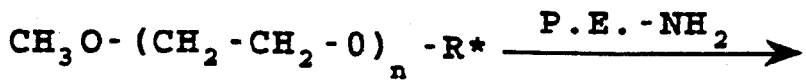
Figure 1:
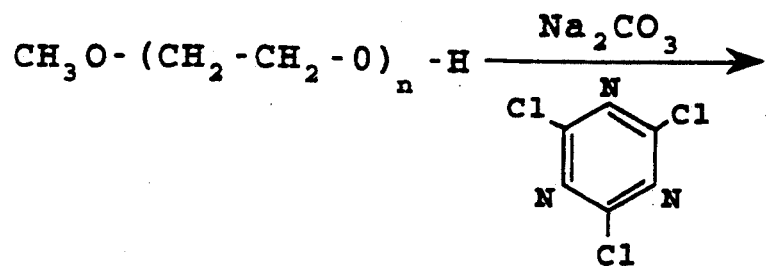

FIG. 1 shows a general reaction scheme for preparing a vesicle-forming lipid derivatized with a biocompatible, hydrophilic polymer, as exemplified by polyethylene glycol (PEG), polylactic acid, and polyglycolic acid, all of which are readily water soluble, can be coupled to vesicle-forming lipids, and are tolerated in vivo without toxic effects. The hydrophilic polymer which is employed, e.g., PEG, is preferably capped by a methoxy, ethoxy or other unreactive group at one end or, alternatively, has a chemical group that is more highly reactive at one end than the other. The polymer is activated at one of its ends by reaction with a suitable activating agent, such as cyanuric acid, diimadozle, anhydride reagent, or the like, as described below. The activated compound is then reacted with a vesicle-forming lipid, such as a diacyl glycerol, including diacyl phosphoglycerols, where the two hydrocarbon chains are typically between 14-22 carbon atoms in length and have varying degrees of saturation, to produce the derivatized lipid. Phosphatidylethanol-amine (PE) is an example of a phospholipid which is preferred for this purpose since it contains a reactive amino group which is convenient for coupling to the activated polymers. Alternatively, the lipid group may be activated for reaction with the polymer, or the two groups may be joined in a concerted coupling reaction, according to known coupling methods. PEG capped at one end with a methoxy or ethoxy group can be obtained commercially in a variety of polymer sizes, e.g., 500-20,000 dalton molecular weights.

The vesicle-forming lipid is preferably one having two hydrocarbon chains, typically acyl chains, and a polar head group. Included in this class are the phospholids, such as phosphatidylcholine (PC), PE, phosphatidic acid (PA), phosphatidylinositol (PI), and sphingomyelin (SM), where the two hydrocarbon chains are typically between about 14–22 carbon atoms in length, and have varying degrees of unsaturation. Also included in this class are the glycolipids, such as cerebrosides and gangliosides.

Another vesicle-forming lipid which may be employed is cholesterol and related sterols. In general, cholesterol may be less tightly anchored to a lipid bilayer membrane, particularly when derivatized with a high molecular weight polymers, such as polyalkylether, and therefore be less effective in promoting liposome evasion of the RES in the bloodstream.

More generally, and as defined herein, "vesicle-forming lipid" is intended to include any amphipathic lipid having hydrophobic and polar head group moieties, and which (a) by itself can form spontaneously into bilayer vesicles in water, as exemplified by phospholipids, or (b) is stably incorporated into lipid bilayers in combination with phospholipids, with its hydrophobic moiety in contact with the interior, hydrophobic region of the bilayer membrane, and its polar head group moiety oriented toward the exterior, polar surface of the membrane. An example of a latter type of vesicle-forming lipid is cholesterol and cholesterol derivatives, such as cholesterol sulfate and cholesterol hemisuccinate.

According to one important feature of the invention, the vesicle-forming lipid may be a relatively fluid lipid, typically meaning that the lipid phase has a relatively low liquid to liquid-crystalline melting temperature, e.g., at or below room temperature, or relatively rigid lipid, meaning that the lipid has a relatively high melting temperature, e.g., up to 60° C. As a rule, the more rigid, i.e., saturated lipids, contribute to greater membrane rigidity in a lipid bilayer structure and also contribute to greater bilayer stability in serum. Other lipid components, such as cholesterol, are also known to contribute to membrane rigidity and stability in lipid bilayer structures. As mentioned above, a long chain (e.g. C-18) saturated lipid plus cholesterol is one preferred composition for delivering anthracycline antibiotic and plant alkaloids anti-tumor agents to solid tumors since these liposomes do not tend to release the drugs into the plasma as they circulate through the bloodstream and enter the tumor during the first 48 hours following injection. Phospholipids whose acyl chains have a variety of degrees of saturation can be obtained commercially, or prepared according to published methods.

Figure 2:
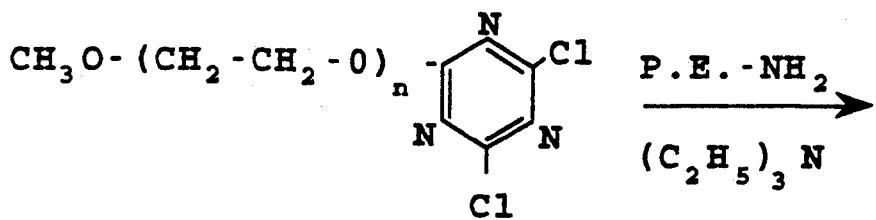
FIG. 2 is a reaction scheme for preparing phosphatidylethanolamine (PE) derivatized with polyethyleneglycol via a cyanuric chloride linking agent.
Figure 2:
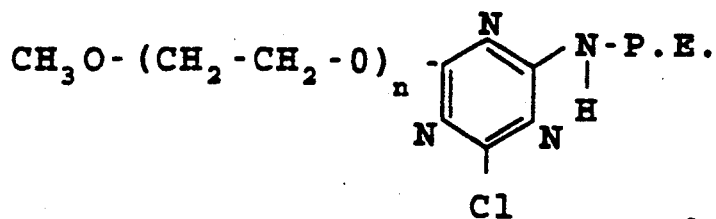

FIG. 2 shows a reaction scheme for producing a PEPEG lipid in which the PEG is derivatized to PE through a cyanuric chloride group. Details of the reaction are provided in Example 1. Briefly, methoxy-capped PEG is activated with cyanuric chloride in the presence in sodium carbonate under conditions which produced the activated PEG compound shown in the figure. This material is purified to remove unreacted cyanuric acid. The activated PEG compound is reacted with PE in the presence of triethyl amine to produce the desired PE-PEG compound shown in the figure. The yield is about 8–10% with respect to initial quantities of PEG.

The method just described may be applied to a variety of lipid amines, including PE, cholesteryl amine, and glycolipids with sugar-amine groups.

Figure 3:
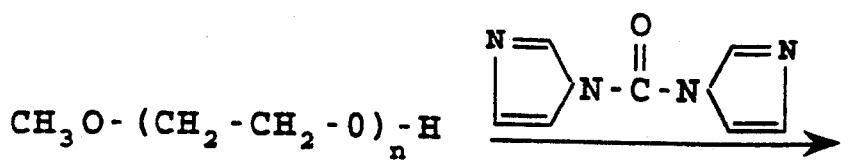
FIG. 3 illustrates a reaction scheme for preparing phosphatidylethanolamine (PE) derivatized with polyethyleneglycol by means of a diimidazole activating reagent.
Figure 3:
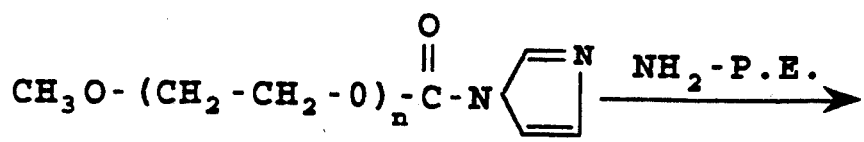
Figure 3:
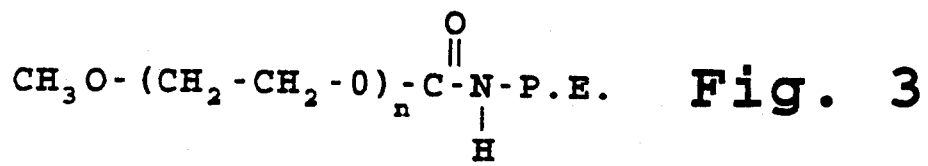

A second method of coupling a polyalkylether, such as capped PEG to a lipid amine is illustrated in FIG. 3. Here the capped PEG is activated with a carbonyl diimidazole coupling reagent, to form the activated imidazole compound shown in FIG. 3. Reaction with a lipid amine, such as PE leads to PEG coupling to the lipid through an amide linkage, as illustrated in the PEG-PE compound shown in the figure. Details of the reaction are given in Example 2.

Figure 4:
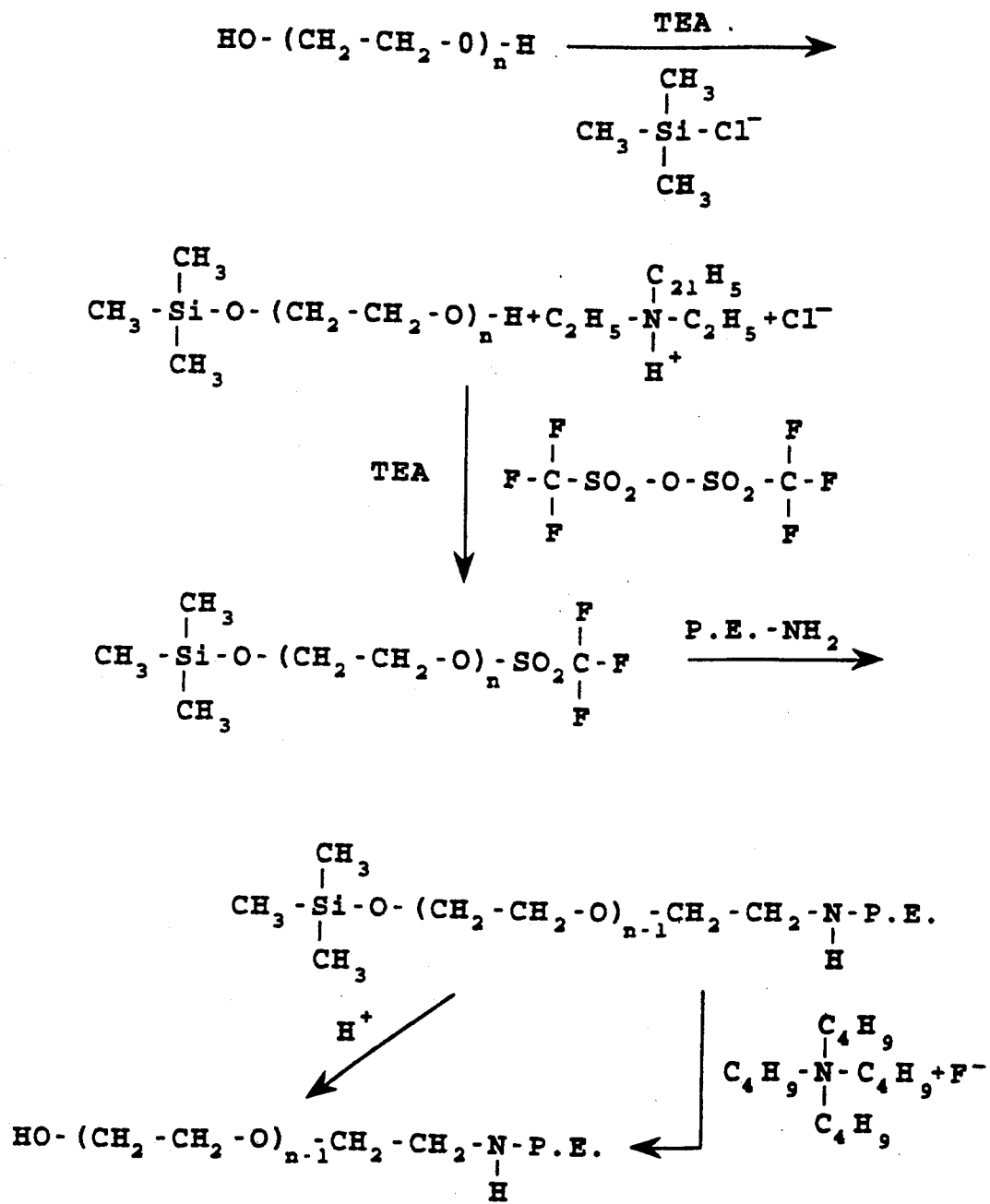
FIG. 4 illustrates a reaction scheme for preparing phosphatidylethanolamine (PE) derivatized with polyethyleneglycol by means of a trifluoromethane sulfonate reagent.

A third reaction method for coupling a capped polyalkylether to a lipid amine is shown in FIG. 4. Here PEG is first protected at its OH end by a trimethylsilane group. The end-protection reaction is shown in the figure, and involves the reaction of trimethylsilylchloride with PEG in the presence of triethylamine. The protected PEG is then reacted with the anhydride of trifluoromethyl sulfonate to form the PEG compound activated with trifluoromethyl sulfonate. Reaction of the activated compound with a lipid amine, such as PE, in the presence of triethylamine, gives the desired derivatized lipid product, such as the PEG-PE compound, in which the lipid amine group is coupled to the polyether through the terminal methylene carbon in the polyether polymer. The trimethylsilyl protective group can be released by acid treatment, as indicated in the figure, or, alternatively, by reaction with a quaternary amine fluoride salt, such as the fluoride salt of tetrabutylamine.

It will be appreciated that a variety of known coupling reactions, in addition to those just described, are suitable for preparing vesicle-forming lipids derivatized with hydrophilic polymers such as PEG, polylactic acid, polyglycolic acid or polylactic-polyglycolic copolymers. For example, the sulfonate anhydride coupling reagent illustrated in FIG. 4 can be used to join an activated polyalkylether to the hydroxyl group of an amphipathic lipid, such as the 5'-OH of cholesterol. Other reactive lipid groups, such as an acid or ester lipid group may also be used for coupling, according to known coupling methods. For example, the acid group of phosphatidic acid can be activated to form an active lipid anhydride, by reaction with a suitable anhydride, such as acetic anhydride, and the reactive lipid can then be joined to a protected polyalkylamine by reaction in the presence of an isothiocyanate reagent.

Figure 5A:
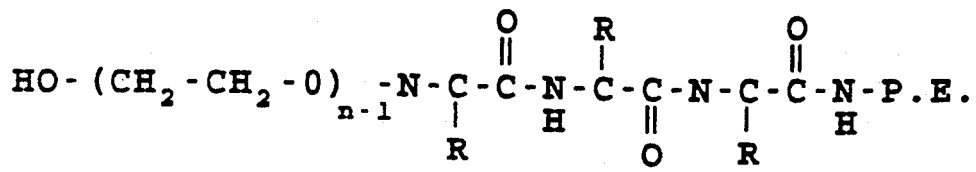
FIG. 5 illustrates a vesicle-forming lipid derivatized with polyethyleneglycol through a peptide (A), ester (B), and disulfide (C) linkage.
Figure 5B:
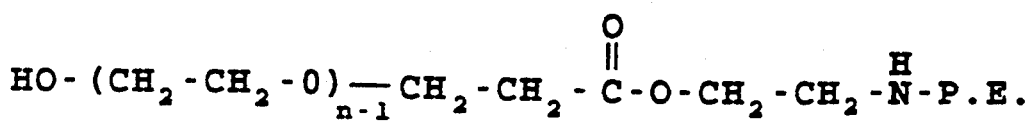
Figure 5C:
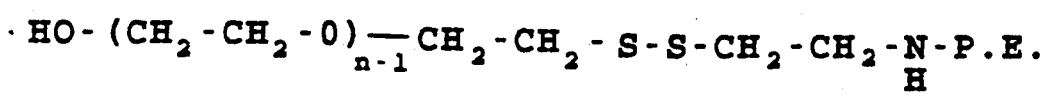

In another embodiment, the derivatized lipid components are prepared to include a labile lipid-polymer linkage, such as a peptide, ester, or disulfide linkage, which can be cleaved under selective physiological conditions, such as in the presence of peptidase or esterase enzymes or reducing agents such as glutathione present in the bloodstream. FIG. 5 shows exemplary lipids which are linked through (A) peptide, (B), ester, and (C), disulfide containing linkages. The peptide-linked compound can be prepared, for example, by first coupling a polyalkylether with the N-terminal amine of the tripeptide shown, e.g., via the reaction shown in FIG. 3. The peptide carboxyl group can then be coupled to a lipid amine group through a carbodiimide coupling reagent conventionally. The ester linked compound can be prepared, for example, by coupling a lipid acid, such as phosphatidic acid, to the terminal alcohol group of a polyalkylether, using alcohol via an anhydride coupling agent. Alternatively, a short linkage fragment containing an internal ester bond and suitable end groups, such as primary amine groups can be used to couple the polyalkylether to the amphipathic lipid through amide or carbamate linkages. Similarly, the linkage fragment may contain an internal disulfide linkage, for use in forming the compound shown at C in FIG. 5. Polymers coupled to phospholipids via such reversible linkages are useful to provide high blood levels of liposomes which contain them for the first few hours post injection. After this period, plasma components cleave the reversible bonds releasing the polymers and the "unprotected" liposomes are rapidly taken up by the RES by the same mechanism as conventional liposomes.

It will be appreciated that the polymers in the derivatized lipids must be (a) safe for parenteral administration, both in terms of toxicity, biodegradability, and tissue compatibility, (b) compatible with stable lipid structure, and (c) amenable to liposome preparation and processing steps. These requirements are met by PEG polymers, and also by the thermoplastic polyester polymers polylactic acid and polyglycolic acid (also referred to as polylactide and polyglycolide) and copolymers of lactide and glycolide such as poly(lactide-co-glycolide). In particular, the polyester polymers are safe to administer because they biodegrade by undergoing random, nonenzymatic, hydrolytic cleavage of their ester linkages to form lactic acid and glycolic acid, which are normal metabolic compounds (Tice and Cowsar, and Wise et al.).

Figure 6:
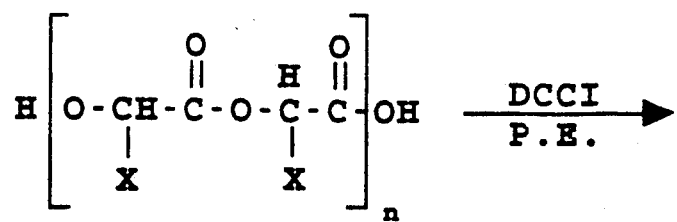
FIG. 6 illustrates a reaction scheme for preparing phosphatidylethanolamine (PE) derivatized with polylactic acid, polyglycolic acids and copolymers of the two.
Figure 6:
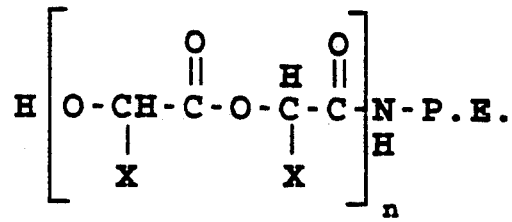

FIG. 6 illustrates a method for derivatizing polylactic acid, polyglycolic acid and polylactic-polyglycolic copolymers with PE. The polylactic acid is reacted, in the presence of PE, with dicyclohexylcarboimide (DCCI), as detailed in Example 2. Similarly, a vesicle-forming lipid derivatized with polyglycolic acid may be formed by reaction of polyglycolic acid or glycolic acid with PE in the presence of a suitable coupling agent, such as DCCI, also as detailed in Example 2. Similar chemistry may be used to form lipid derivatives of polylactic-polyglycolic copolymers. The vesicleforming lipids derivatized with either polylactic acid or polyglycolic acid and their copolymers form part of the invention herein. Also forming part of the invention are liposomes containing these derivatized lipids, in a 1–20 mole percent.

II. Preparation of Liposome Composition

A. Lipid Components

The lipid components used in forming the liposomes of the invention may be selected from a variety of vesicle-forming lipids, typically including phospholipids, sphingolipids and sterols. As will be seen, one requirement of the liposomes of the present invention is long blood circulation lifetime. It is therefore useful to establish a standardized measure of blood lifetime which can be used for evaluating the effect of lipid components on blood halflife.

One method used for evaluating liposome circulation time in vivo measures the distribution of IV injected liposomes in the bloodstream and the primary organs of the RES at selected times after injection. In the standardized model which is used herein, RES uptake is measured by the ratio of total liposomes in the bloodstream to total liposomes in the liver and spleen, the principal organs of the RES. In practice, age and sex matched mice are injected IV through the tail vein with a radiolabeled liposome composition, and each time point is determined by measuring total blood and combined liver and spleen radiolabel counts, as detailed in Example 5.

Since the liver and spleen account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were calculated at 1,2, 3, 4, and 24 hours post injection.

The liposomes of the present invention include 1–20 mole percent of the vesicle-forming lipid derivatized with a hydrophilic polymer, described in Section I. According to one aspect of the invention, it has been discovered that blood circulation halflives in these liposomes is largely independent of the degree of saturation of the phospholipid components making up the liposomes. That is, the phospholipid components may be composed of predominantly of fluidic, relatively unsaturated, acyl chains, or of more saturated, rigidifying acyl chain components. This feature of the invention is seen in Example 6, which examines blood/RES ratios in liposomes formed with PEG-PE, cholesterol, and PC having varying degrees of saturation (Table 4). As seen from the data in Table 5 in the example, high blood/RES ratios were achieved in substantially all of the liposome formulations, independent of the extent of lipid unsaturation in the bulk PC phospholipid, and no systematic trend, as a function of degree of lipid saturation, was observed.

Accordingly, the vesicle-forming lipids may be selected to achieve a selected degree of fluidity or rigidity, to control the stability of the liposomes in serum and the rate of release of entrapped drug from the liposomes in the bloodstream and/or tumor. The vesicle-forming lipids may also be selected, in lipid saturation characteristics, to achieve desired liposome preparation properties. It is generally the case, for example, that more fluidic lipids are easier to formulate and down-size by extrusion and homogenization methods than more rigid lipid compositions.

Similarly, it has been found that the percentage of cholesterol in the liposomes may be varied over a wide range without significant effect on observed blood/RES ratios. The studies presented in Example 7A, with reference to Table 6 therein, show virtually no change in blood/RES ratios in the range of cholesterol between 0–30 mole percent.

It has also been found, in studies conducted in support of the invention, that blood/RES ratios are also relatively unaffected by the presence of charged lipid components, such as phosphatidylglycerol (PG). This can be seen from FIG. 7, which plots percent loss of encapsulated marker for PEG-PE liposomes containing either 4.7 mole percent PG (triangles) or 14 mole percent PG (circles). Virtually no difference in liposome retention in the bloodstream over a 24 hour period was observed. The option of including negative charge in the liposome without aggravating RES uptake provides a number of potential advantages. Liposomes suspensions which contain negative charge tend to be less sensitive to aggregation in high ionic strength buffers and hence physical stability is enhanced. Also, negative charge present in the liposome membrane can be used as a formulation tool to effectively bind high amounts of cationic drugs.

The vesicle-forming lipid derivatized with a hydrophilic polymer is present in an amount preferably between about 1-20 mole percent, on the basis of moles of derivatized lipid as a percentage of total moles of vesicle-forming lipids. It will be appreciated that a lower mole ratio, such as 0.1 mole percent, may be appropriate for a lipid derivative with a large molecular weight polymer, such as one having a molecular weight of 100 kilodaltons. As noted in Section I, the hydrophilic polymer in the derivatized lipid preferably has a molecular weight between about 200-20,000 daltons, and more preferably between about 1,000-5,000 daltons. Example 7B, which examines the effect of very short ethoxy ether moieties on blood/RES ratios indicates that polyether moieties of greater than about 5 carbon ethers are required to achieve significant enhancement of blood/RES ratios.

B. Preparing the Liposome Composition

The liposomes may be prepared by a variety of techniques, such as those detailed in Szoka et al, 1980. One method for preparing drug-containing liposomes is the reverse phase evaporation method described by Szoka et al and in U.S. Pat. No. 4,235,871. The reverse phase evaporation vesicles (REVs) have typical average sizes between about 2-4 microns and are predominantly oligolamellar, that is, contain one or a few lipid bilayer shells. The method is detailed in Example 4A.

Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium, as detailed in Example 4B. The lipid film hydrates to form MLVs, typically with sizes between about 0.1 to 10 microns.

In accordance with one important aspect of the invention, the liposomes are prepared to have substantially homogeneous sizes in a selected size range between about 0.07 and 0.12 microns. In particular, it has been discovered that liposomes in this size range are readily able to extravasate into solid tumors, as discussed in Section III below, and at the same time, are capable of carrying a substantial drug load to a tumor (unlike small unilamellar vesicles of less than 0.07 $\mu$, which are severely restricted in drug-loading capacity).

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. This method of liposome sizing is used in preparing homogeneous-size REV and MLV compositions described in the examples below. A more recent method involves extrusion through an asymmetric ceramic filter. The method is detailed in U.S. Pat. No. 4,737,323 for Liposome Extrusion issued Apr. 12, 1988. Homogenization methods are also useful for down-sizing liposomes to sizes of 100 nm or less (Martin).

C. Compound Loading

In one embodiment, the composition of the invention is used for localizing an imaging agent, such as radioisotopes including $^{67}$Ga and $^{111}$In, or paramagnetic compounds at the tumor site. In this application, where the radiolabel can be detected at relatively low concentration, it is generally sufficient to encapsulate the imaging agent by passive loading, i.e., during liposome formation. This may be done, for example, by hydrating lipids with an aqueous solution of the agent to be encapsulated. Typically radiolabeled agents are radioisotopic metals in chelated form, such as $^{67}$Ga-desferal, and are retained in the liposomes substantially in entrapped form. After liposome formation and sizing, non-encapsulated material may be removed by one of a variety of methods, such as by ion exchange or gel filtration chromatography. The concentration of chelated metal which can be achieved by passive loading is limited by the concentration of the agent in the hydrating medium.

Active loading of radioimaging agents is also possible by entrapping a high affinity, water soluble chelating agent (such as EDTA or desferoxamine) within the aqueous compartment of liposomes, removing any unentrapped chelating agent by dialysis or gel exclusion column chromatography and incubating the liposomes in the presence of the metal radioisotope chelated to a lower affinity, lipid soluble chelating agent such as 8-hydroxyquinoline. The metal radioisotope is carried into the liposome by the lipid soluble chelating agent. Once in the liposome, the radioisotope is chelated by the entrapped, water soluble chelating agent—effectively trapping the radioisotope in the liposome interior (Gabizon).

Passive loading may also be employed for the amphipathic anti-tumor compounds, such as the alkaloids vinblastine and vincristine, which are therapeutically active at relatively low drug doses, e.g., about 1-15 mg/m$^2$. Here the drug is either dissolved in the aqueous phase used to hydrate the lipid or included with the lipids in liposome formation process, depending on the solubility of the compound. After liposome formation and sizing, free (unbound) drug can be removed, as above, for example, by ion exchange or gel exclusion chromatographic methods.

Where the anti-tumor compound includes a peptide or protein drug, such as interleukin-2 (IL-2) or tissue necrosis factor (TNF), or where the liposomes are formulated to contain a peptide immunomodulator, such as muramyl di- or tri-peptide derivatives or a protein immunomodulator such as macrophage colony stimulating factor (M-CSF), the liposomes are preferably prepared by the above reverse phase method, by a solvent injection system, such as described in U.S. Pat. No. 4,752,425, or by rehydrating a freeze dried mixture of the protein and a suspension of small unilamellar vesicles with water (Kirby). Both methods combine passive loading with relatively high encapsulation efficiency, e.g., up to 50% efficiency. Nonencapsulated material can be readily removed from the liposome suspension, e.g., by dialysis, diafiltration or exclusion chromatography.

The concentration of hydrophobic drug which can be accommodated in the liposomes will depend on drug/lipid interactions in the membrane, but is generally limited to a drug concentration of less than about 20 $\mu$g drug/mg lipid. More specifically, for a variety of anthracycline antibiotics, such as doxorubicin and epirubicin, the highest concentration of encapsulated material which can be achieved by passive loading into the aqueous compartment of the liposome is about 10–20 μg/μmoles lipid (due to the low intrinsic water solubility of these compounds). When 20–30 mole percent of an anionic phospholipid such as PG is included in the liposome membrane, the loading factor can be increased to a maximum of about 40 μg/μmole lipid because the anthracyclines are positively charged and form an "ion pair" complex with the negatively charged PG at the membrane interface (Gabizon, 1988). However, such charged complexed anthracycline formulations have limited utility in the context of the present invention (which requires that the drug be carried through the bloodstream for the first 24–48 hours following IV administration in liposome entrapped form) because the drugs tend to be rapidly released from the liposome membrane in vivo by immediate plasma-induced release and delayed release accompanying RES uptake and processing (Storm, 1987, and Gabizon, 1989).

In accordance with another aspect of the invention, it has been found essential, for delivery of an therapeutically effective dose of a variety of amphipathic antitumor drugs to tumors, to load the liposomes to a high drug concentration by active drug loading methods. For example, for anthracycline antibiotic drugs, such as doxorubicin, epirubicin, daunorubicin, carcinomycin, N-acetyladriamycin, rubidazone, 5-imidodaunomycin, and N-acetyldaunomycin, a final concentration of liposome-entrapped drug of greater than about 25 μg/μmole lipid and preferably 50 μg/μmole lipid or greater is desired. Internal drug concentrations as high as 100–200 μg/μmole lipid are contemplated.

One method for active loading of amphipathic drugs into liposomes is described in co-owned U.S. Pat. application Ser. No. 413,037, filed Sep. 28, 1988. In this method, liposomes are prepared in the presence of a relatively high concentration of ammonium ion, such as 0.125 M ammonium sulfate. After sizing the liposomes to a desired size, the liposome suspension is treated to create an inside-to-outside ammonium ion gradient across the liposomal membranes. The gradient may be created by dialysis or diafiltration against a non-ammonium containing medium, such as an isotonic glucose medium, or by gel filtration, such as on a Sephadex G-50 column equilibrated with 0.15 M NaCl or KCl, effectively replacing ammonium ions in the exterior phase with sodium or potassium ions. Alternatively, the liposome suspension may be diluted with a non-ammonium solution, thereby reducing the exterior-phase concentration of ammonium ions. The ammonium concentration inside the liposomes is preferably at least 10 times, and more preferably at least 100 to 1000 times that in the external liposome phase.

The ammonium ion gradient across the liposomes in turn creates a pH gradient, as ammonia is released across the liposome membrane, and protons are trapped in the internal aqueous phase of the liposome. To load liposomes with the selected drug a suspension of the liposomes, e.g., about 20–200 mg/ml lipid, is mixed with an aqueous solution of the drug, and the mixture is allowed to equilibrate over an period of time, e.g., several hours, at temperatures ranging from room temperature to 60° C.—depending on the phase transition temperature of the lipids used to form the liposome. In one typical method, a suspension of liposomes having a lipid concentration of 50 μmoles/ml is mixed with an equal volume of anthracycline drug at a concentration of about 5–8 mg/ml. At the end of the incubation period, the suspension is treated to remove free (unbound) drug. One preferred method of drug removal for anthracycline drugs is by passage over an ion exchange resin, such as Dowex 50 WX-4, which is capable of binding unencapsulated drug, but not liposomes containing the drug.

Although, as noted above, the plant alkaloids such as vincristine do not require high loading factors in liposomes due to their intrinsically high anti-tumor activity, and thus can be loaded by passive entrapment techniques, it also possible to load these drug by active methods. Since vincristine is amphipathic and a weak base, it and similar molecules can be loaded into liposomes using a pH gradient formed by entrapping ammonium sulfate as described above for the anthracycline antibiotics.

The remote loading method just described is illustrated in Example 10, which describes the preparation of 0.1 micron liposomes loaded with doxorubicin, to a final drug concentration of about 80–100 μg/μmoles lipid. The liposomes show a very low rate of drug leakage when stored at 4° C.

III. Liposome Localization in Solid Tumors

A. Extended Bloodstream Halflife

One of the requirements for liposome localization in a target tumor, in accordance with the invention, is an extended liposome lifetime in the bloodstream following IV liposome administration. One measure of liposome lifetime in the bloodstream in the blood/RES ratio determined at a selected time after liposome administration, as discussed above. Blood/RES ratios for a variety of liposome compositions are given in Table 3 of Example 5. In the absence of PEG-derivatized lipids, blood/RES ratios were 0.03 or less. In the presence of PEG-derivatized lipids, the blood/RES ratio ranged from 0.2, for low-molecular weight PEG, to between 1.7–4 for several of the formulations, one of which lacks cholesterol, and three of which lack an added charged phospholipid (e.g., PG).

The data presented in Table 5 in Example 6 show blood/RES ratios (excluding two points with low percent recovery) between about 1.26 and 3.27, consistent with the data given in Table 3. As noted in Section II above, the blood lifetime values are substantially independent of degree of saturation of the liposome lipids, presence of cholesterol and presence of charged lipids.

The blood/RES values reported above can be compared with blood/RES values reported in co-owned U.S. Pat. No. 4,920,016, which used blood/RES measurement methods similar to those used in generating the data presented in Tables 3 and 5. The best 24-hour blood/RES ratios which were reported in the above-noted patent was 0.9, for a formulation composed of $GM_1$, saturated PC, and cholesterol. The next best formulations gave 24-hour blood/RES values of about 0.5. Thus, typical 24-hour blood/RES ratios obtained in a number of the current formulations were more than twice as high as the best formulations which have been reported to date. Further, ability to achieve high blood/RES with $GM_1$ or HPI lipids was dependent on the presence of predominantly saturated lipids and cholesterol in the liposomes.

Figure 7:
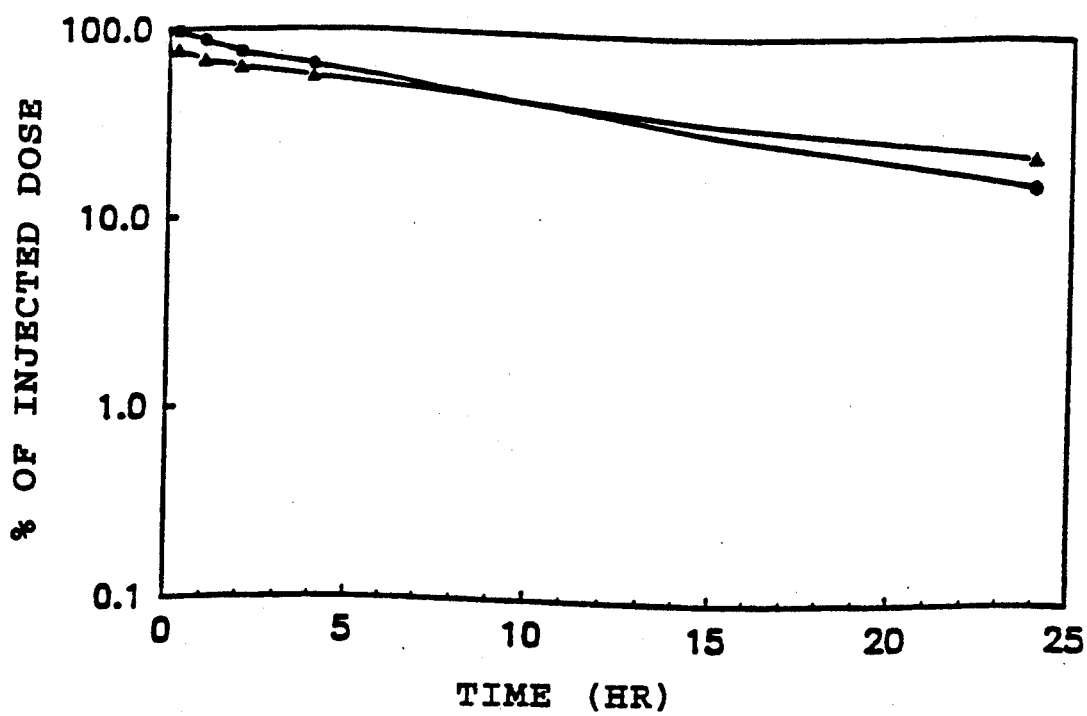
FIG. 7 is a plot of liposome residence times in the blood, expressed in terms of percent injected dose as a function of hours after IV injection, for PEG-PE liposomes containing different amounts of phosphatidylglycerol.
Figure 8:
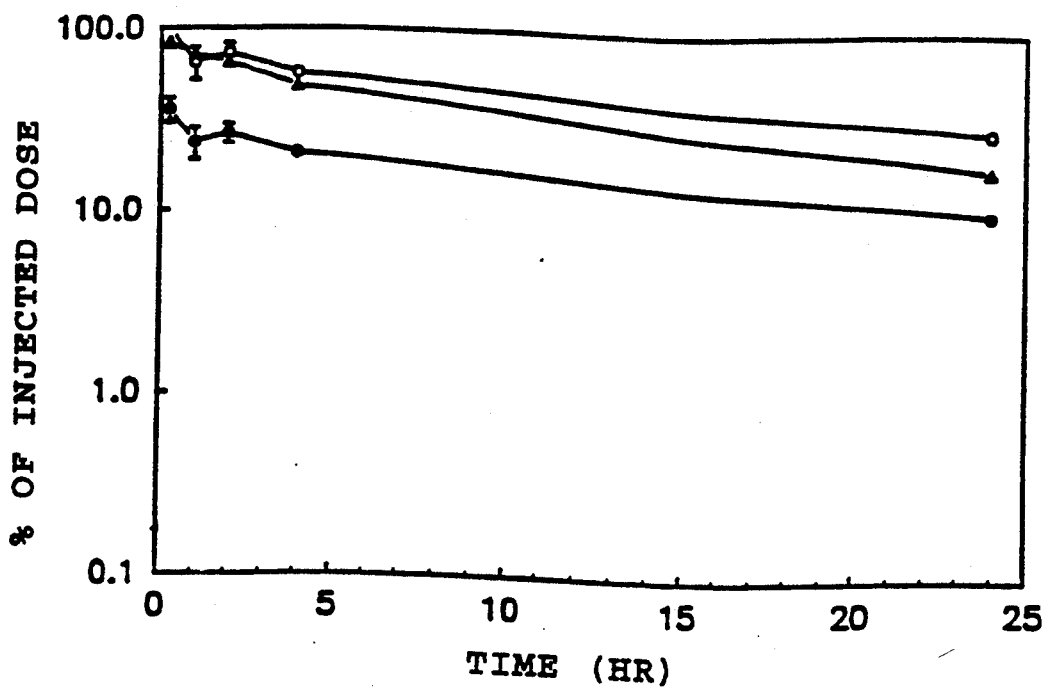
FIG. 8 is a plot similar to that of FIG. 7, showing blood residence times of liposomes composed of predominantly unsaturated phospholipid components.

Plasma pharmacokinetics of a liposomal marker in the bloodstream can provide another measure of the enhanced liposome lifetime which is achieved by the liposome formulations of the present invention. FIG. 7 and 8 discussed above show the slow loss of liposomal marker from the bloodstream over a 24 hour period in typical PEG-liposome formulations, substantially independent of whether the marker is a lipid or an encapsulated watersoluble compound (FIG. 8). In both plots, the amount of liposomal marker present 24 hours after liposome injection is greater than 10% of the originally injected material.

Figure 9:
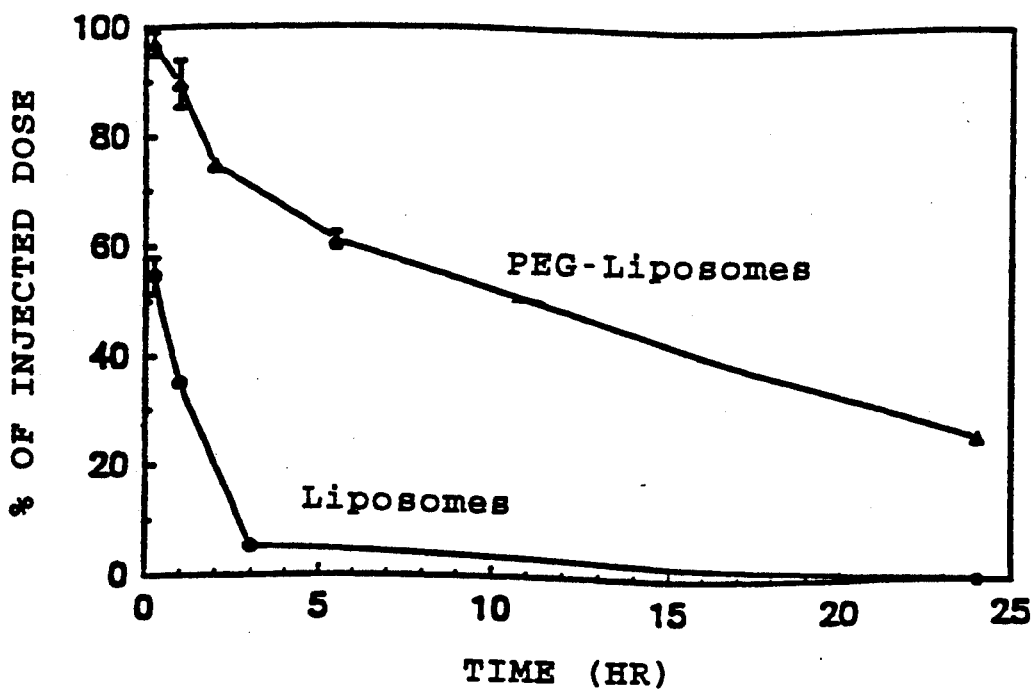
FIG. 9 is a plot similar to that of FIG. 7, showing the blood residence times of PEG-coated liposomes (solid triangles) and conventional, uncoated liposomes (solid circles)

FIG. 9 shows the kinetics of liposome loss from the bloodstream for a typical PEG-liposome formulation and the same liposomes in the absence of a PEG-derivatized lipid. After 24 hours, the percent marker remaining in the PEG-liposomes was greater than about 20%, whereas the conventional liposomes showed less than 5% retention in the blood after 3 hours, and virtually no detectable marker at 24 hours.

The results seen in FIGS. 7-9 are consistent with 24 hour blood liposome values measured for a variety of liposome formulations, and reported in Tables 3 and 5-7 in Example 5-8 below. As seen in Table 3 in Example 5, the percent dose remaining at 24 hours was less than 1% for conventional liposomes, versus at least 5% for the PEG-liposomes. In the best formulations, values between about 20-40% were obtained. Similarly in Table 5 from Example 6, liposome levels in the blood after 24 hours (again neglecting two entries with low recovery values) were between 12 and about 25 percent of total dose given. Similar results are reported in Tables 6 and 7 of Example 7.

Figure 11:
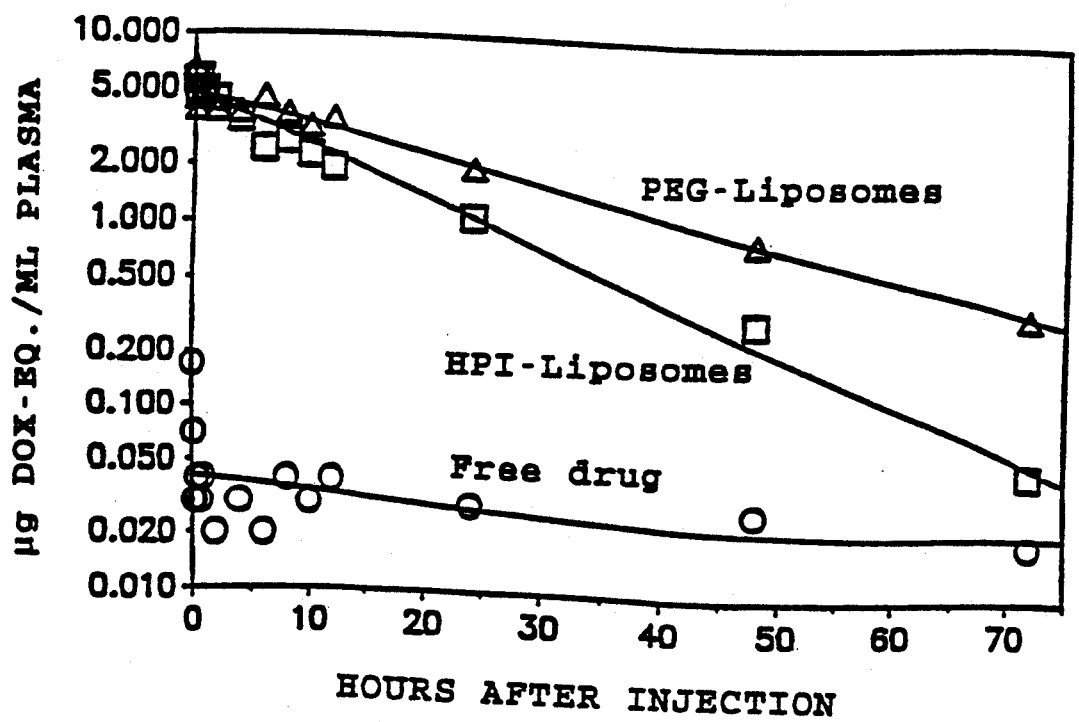
FIG. 11 is a plot showing the kinetics of doxorubicin clearance from the blood of beagle dogs, for drug administered IV in free form (open circles), in liposomes formulated with saturated phospholipids and hydrogenated phosphatidylinositol (HPI) (open squares), and in liposomes coated with PEG (open triangles)

The ability of the liposomes to retain an amphipathic anti-tumor drug while circulating in the bloodstream over the 24-48 period post injection required to provide an opportunity for the liposome to reach and enter a systemic tumor has also been investigated. In the study reported in Example 11, the plasma pharmacokinetics of doxorubicin loaded in PEG-liposomes, doxorubicin given in free form, and doxorubicin loaded into liposomes containing hydrogenated phosphatidylinositol (HPI) was invested in beagle dogs, a species which closely correlates with man in this respect. The HPI liposomes were formulated with a predominantly saturated PC lipid and cholesterol, and represents one of the optimal formulations described in the above co-owned U.S. patent. The kinetics of doxorubicin in the blood up to 72 hours after drug administration is shown in FIG. 11. Both liposomal formulations showed single-mode exponential loss of drug, in contrast to free drug which shows a biexponential pattern. However, the amount of drug retained in the bloodstream at 72 hours was about 8-10 times greater in the PEG-liposomes compared with the PI liposomes.

For both blood/RES ratios, and liposome retention time in the bloodstream, the data obtained from a model animal system can be reasonably extrapolated to humans and veterinary animals of interest. This is because uptake of liposomes by liver and spleen has been found to occur at similar rates in several mammalian species, including mouse, rat, monkey, and human (Gregoriadis, 1974; Jonah; Kimelberg, 1976; Juliano; Richardson; Lopez-Berestein). This result likely reflects the fact that the biochemical factors which appear to be most important in liposome uptake by the RES—including opsinization by serum lipoproteins, size-dependent uptake effects, and cell shielding by surface moieties—are common features of all mammalian species which have been examined.

B. Extravasation into Tumors

Another required feature for high-activity liposome targeting to a solid tumor, in accordance with the invention, is liposome extravasation into the tumor through the endothelial cell barrier and underlying basement membrane separating a capillary from the tumor cells supplied by the capillary. This feature is optimized in liposomes with sizes between about 0.07 and 0.12 microns. Although liposomes with sizes of less than 0.7 microns would also be expected to extravasate, the severely limiting drug-carrying capacity of these small liposomes would render them ineffective as drug carriers for the present system. For the purposes of the present invention, then, the optimal size range for liposomes would strike a balance between ability to extravasate and drug-carrying capacity, that is, between 0.07 and 0.12 microns in diameter.

Figure 12A:
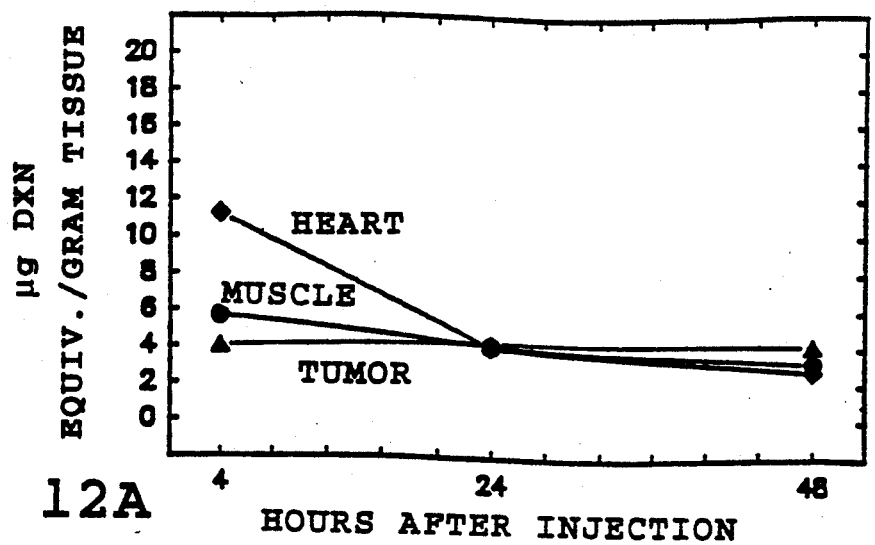
FIGS. 12A and 12B are plots of the time course of doxorubicin uptake from the bloodstream by heart (solid diamonds), muscle (solid circles), and tumor (solid triangles) for drug administered IV in free (12A) and PEG-liposomal (12B) form.

That liposome delivery to the tumor is required for selective drug targeting can be seen from the study reported in Example 12. Here mice were inoculated subcutaneously with the J-6456 lymphoma which formed a solid tumor mass of about 1 cm$^3$ after one-two weeks. The animals were then injected either with free doxorubicin or doxorubicin loaded into PEG-liposomes at a dose of 10 mg drug per kg body weight. The tissue distribution (heart, muscle, and tumor) of the drug was then assayed at 4, 24, and 48 hours after drug administration. FIG. 12A shows the results obtained for free drug. No selective drug accumulation into the tumor occurred, and in fact, the highest initial drug levels were in the heart, where greatest toxicity would be produced.

By contrast, drug delivery in PEG-liposomes showed increasing drug accumulation into the tumor between 4-24 hours, and high selective tumor levels between 24 and 48 hours. Drug uptake by both heart and muscle tissue was, by contrast, lower than with free drug. As seen from the data plotted in FIG. 12B, the tumor contained 8 times more drug compared with healthy muscle and 6 times the amount in heart at 24 hours post injection.

To confirm that the PEG-liposomes deliver more antitumor drug to a intraperitoneal tumor, groups of mice were injected IP with 10$^6$ J-6456 lymphoma cells. After five days the IP tumor had been established, and the animals were treated IV with 10 mg/kg doxorubicin, either in free drug form or entrapped in PEG-containing liposomes. Tissue distribution of the drug is tabulated in Table 9, Example 12. As shown, the tumor/heart ratio was about 272 greater for liposome delivery than for free drug at 24 hours, and about 47 times greater at 48 hours.

Figure 13:
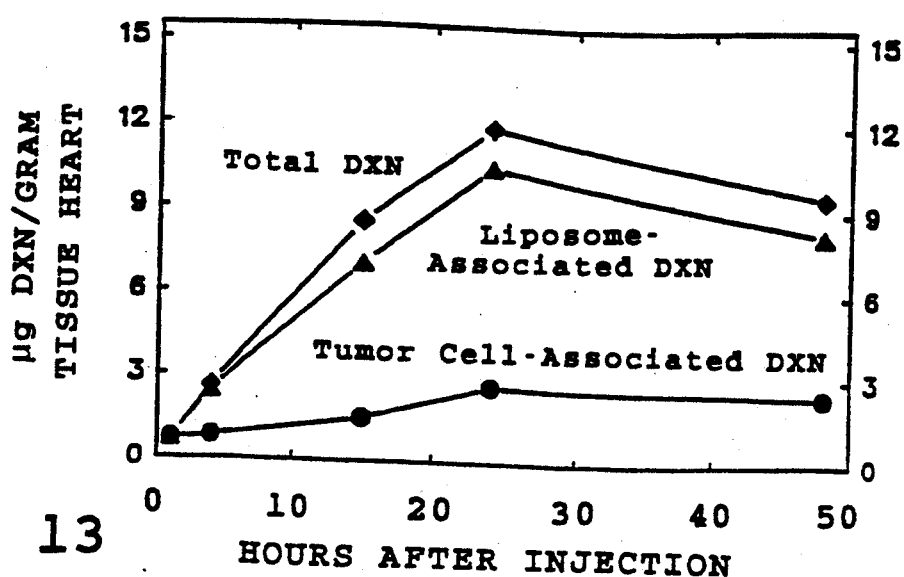
FIG. 13 is a plot of the time course of uptake of doxorubicin from the bloodstream by J-6456 tumor cells implanted interperitoneally (IP) in mice, as measured as total drug (filled diamonds) as drug associated with tumor cells (solid circles) and liposome-associated form (solid triangles)

To demonstrate that the results shown in Table 9 are due to the entry of intact liposomes into the extravascular region of a tumor, the tumor tissue was separated into cellular and supernatant (intercellular fluid) fractions, and the presence of liposome-associated and free drug in both fractions was assayed. FIG. 13 shows the total amount of drug (filled diamonds) and the amount of drug present in tumor cells (solid circles) and supernatant (solid diamonds) over a 48-hour post injection period. To assay liposome-associated drug, the supernatant was passed through an ion-exchange resin to remove free drug (Gabizon, 1989), and the drug remaining in the supernatant was assayed (solid triangles). As seen, most of the drug in the tumor is liposome-associated.

Further demonstration of liposome extravasation into tumor cells was obtained by direct microscopic observation of liposome distribution in normal liver tissue and in solid tumors, as detailed in Example 14. FIG.

14A shows the distribution of liposomes (small, darkly stained bodies) in normal liver tissue 24 hours after IV injection of PEG-liposomes. The liposomes are confined exclusively to the Kupfer cells and are not present either in hepatocytes or in the intercellular fluid of the normal liver tissue.

Figure 14A:
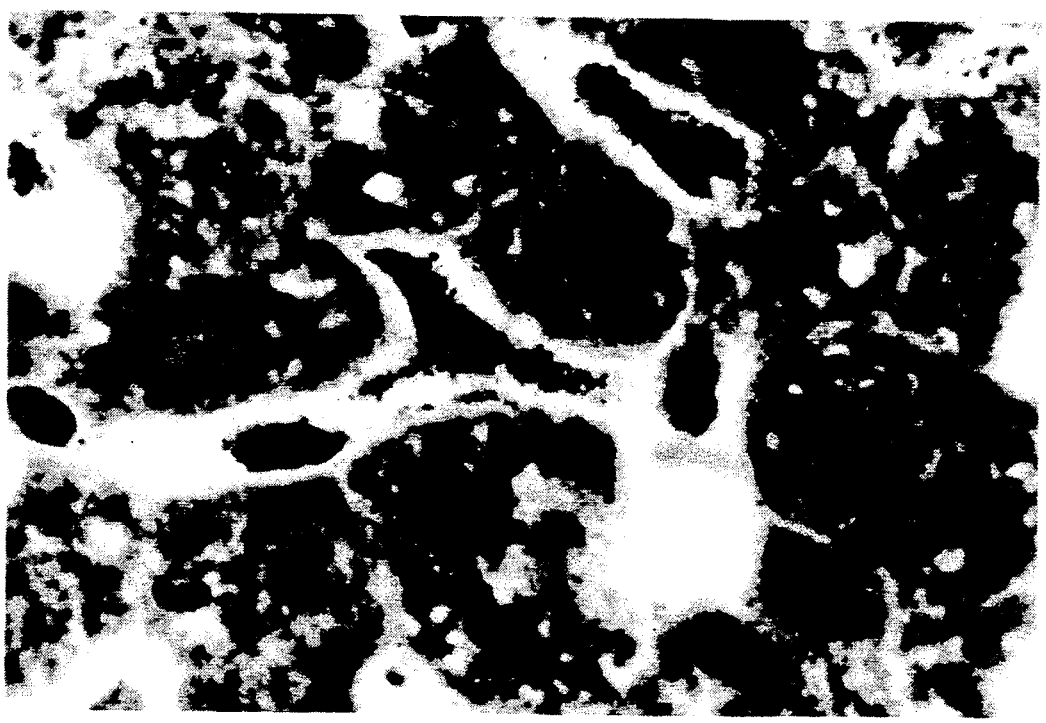
FIGS. 14A-14D are light micrographs showing localization of liposomes (small dark stained particles) in Kupfer cells in normal liver (14A), in the interstitial fluid of a C-26 colon carcinoma implanted in liver in the region of a capillary supplying the tumor cells (14B) and in the region of actively dividing C-26 tumor cells implanted in liver (14C) or subcutaneously (14D)
Figure 14B:
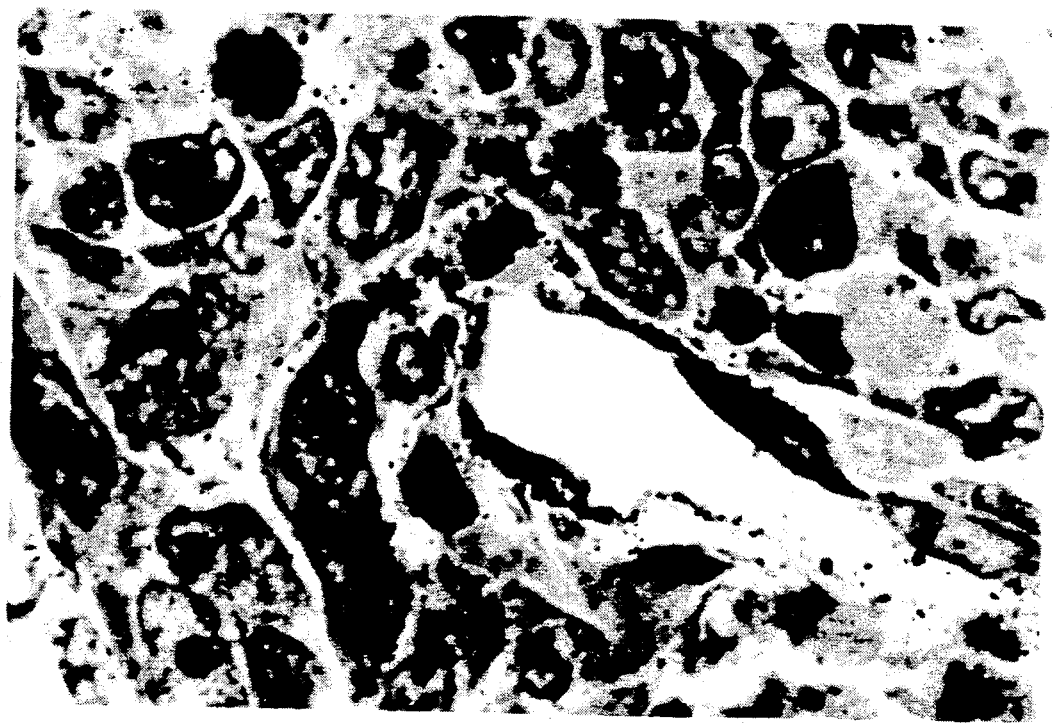

FIG. 14B shows a region of C-26 colon carcinoma implanted in the liver of mice, 24 hours after injection of PEG-liposomes. Concentrations of liposomes are clearly evident in the region of the capillary in the figure, on the tumor tissue side of the endothelial barrier and basement membrane. Liposomes are also abundant in the intercellular fluid of the tumor cells, further evidencing passage from the capillary lumen into the tumor. The FIG. 14C photomicrograph shows another region of the tumor, where an abundance of liposomes in the intercellular fluid is also evident. A similar finding was made with liposome extravasation into a region of C-26 colon carcinoma cells injected subcutaneously, as seen in FIG. 14D.

IV. Tumor Localization Method

As detailed above, the liposomes of the invention are effective to localize an anti-tumor drug specifically in a solid tumor region by virtue of the extended lifetime of the liposomes in the bloodstream and a liposome size which allows both extravasation into tumors, a relatively high drug carrying capacity and minimal leakage of the entrapped drug during the time required for the liposomes to distribute to and enter the tumor (the first 24-48 hours following injection). The liposomes thus provide an effective method for localizing a compound selectively to a solid tumor, by entrapping the compound in such liposomes and injecting the liposomes IV into a subject. In this context a "solid" tumor is defined as one that grows in an anatomical site outside the bloodstream (in contrast, for example, to blood-born tumors such as leukemias) and requires the formation of small blood vessels and capillaries to supply nutrients, etc. to the growing tumor mass. In this case, for an IV injected liposome (and its entrapped anti-tumor drug) to reach the tumor site it must leave the bloodstream and enter the tumor. In one embodiment, the method is used for tumor treatment by localizing an anti-tumor drug selectively in the tumor. The anti-tumor drug which may be used is any compound, including the ones listed below, which can be stably entrapped in liposomes at a suitable loading factor and administered at a therapeutically effective dose (indicated below in parentheses after each compound). These include amphipathic anti-tumor compounds such as the plant alkaloids vincristine (1.4 mg/m$^2$), vinblastine (4-18 mg/m$^2$) and etoposide (35-100 mg/m$^2$), and the anthracycline antibiotics including doxorubicin (60-75 mg/m$^2$), epirubicin (60-120 mg/m$^2$) and daunorubicin (25-45 mg/m$^2$). The water-soluble anti-metabolites such as methotrexate (3 mg/m$^2$), cytosine arabinoside (100 mg/m$^2$), and fluorouracil (10-15 mg/kg), the antibiotics such as bleomycin (10-20 units/m$^2$), mitomycin (20 mg/m$^2$), plicamycin (25-30 $\mu$g/$^2$) and dactinomycin (15 $\mu$g/m$^2$), and the alkylating agents including cyclophosphamide (3-25 mg/kg), thiotepa (0.3-0.4 mg/Kg) and BCNU (150-200 mg/m$^2$) are also useful in this context. As noted above, the plant alkaloids exemplified by vincristine and the anthracycline antibiotics including doxorubicin, daunorubicin and epirubicin are preferably actively loaded into liposomes, to achieve drug/lipid ratios which are several times greater than can be achieved with passive loading techniques. Also as noted above, the liposomes may contain encapsulated tumor-therapeutic peptides and protein drugs, such as IL-2, and/or TNF, and/or immunomodulators, such as M-CSF, which are present alone or in combination with anti-tumor drugs, such as an anthracycline antibiotic drug.

The ability to effectively treat solid tumors, in accordance with the present invention, has been shown in a variety of in vivo systems. The method reported in Example 15 compares the rate of tumor growth in animals implanted subcutaneously with a C-26 colon carcinoma. Treatment was with epirubicin, either in free form, or entrapped in PEG-liposomes, in accordance with the invention, with the results shown in FIGS. 15A-C. As seen, and discussed more fully in Example 15, treatment with epirubicin loaded PEG-liposomes produced a marked suppression of tumor growth and lead to long term survivors among groups of animals inoculated with a normally lethal dose of tumor cells.

Significantly, in this tumor model of colon carcinoma, anthracyclines such as epirubicin and doxorubicin which show in vitro activity against this tumor, fail to produce any responses in vivo in free form or when administered in conventional liposomes. Details are given in Example 18, with reference to FIG. 17. In sharp contrast, delayed treatment of animals with the epirubicin loaded PEG liposomes resulted in regression of established subcutaneous tumors of a size that would be easily detectable in man. This closely resembles a clinical situation in which a patient's tumor has reached a size of 1-2 cm$^3$ before detection.

Figure 16:
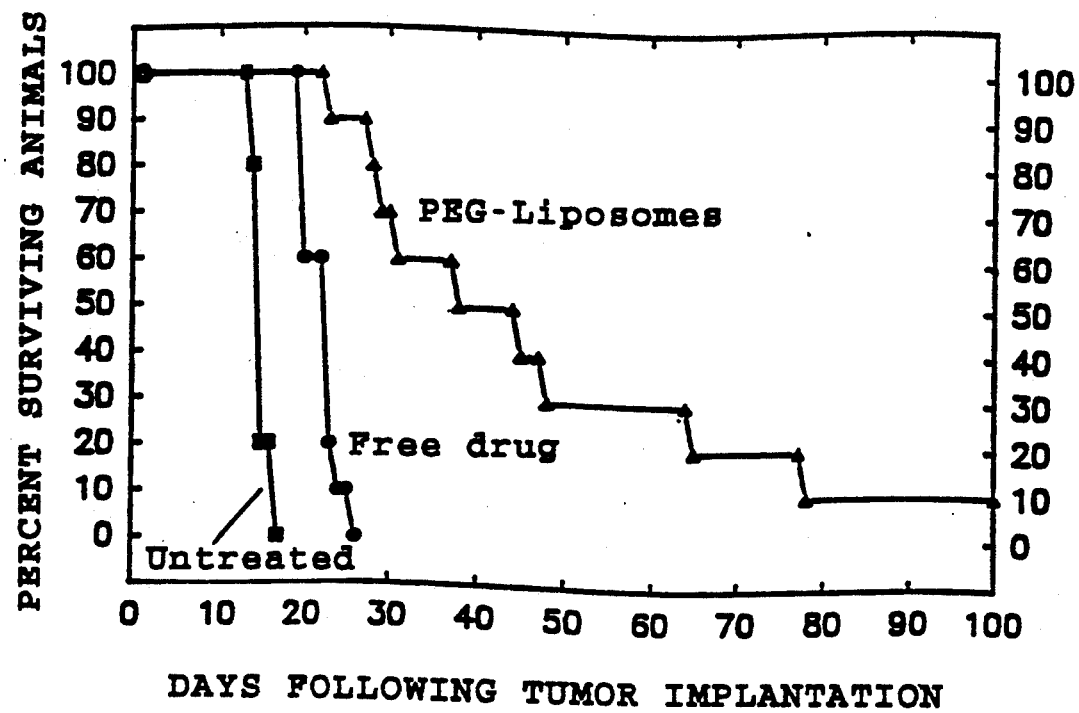
FIG. 16 is a plot showing percent survivors, in days following interperitoneal implantation of a J-6456 lymphoma, for animals treated with doxorubicin in free form (closed circles) or PEG-liposomal form (solid triangles), or untreated animals (open triangles)

Similar results were obtained for treatment of a lymphoma implanted interperitoneally in mice, as detailed in Example 16. Here the animals were treated with doxorubicin in free form or entrapped in PEG-liposomes. Percent survivors over a 100-day period following tumor implantation and drug treatment is shown in FIG. 16. The results are similar to those obtained above, showing marked increase in the median survival time and percent survivors with PEG-liposomes over free drug treatment.

Since reduced toxicity has been observed in model animal systems and in a clinical setting in tumor treatment by doxorubicin entrapped in conventional liposomes (as reported, for example, in U.S. Pat. No. 4,797,285), it is of interest to determine the degree of toxicity protection provided in the tumor treatment method of the present invention. In the study reported in Example 17, animals were injected IV with increasing doses of doxorubicin or epirubicin in free form or entrapped in conventional or PEG-liposomes. The maximum tolerated dose (MTD) for the various drug formulations is given in Table 10 in the Example. For both drugs, entrapment in PEGliposomes approximately doubled the MTD of the drug. Similar protection was achieved with conventional liposomes.

Figure 17:
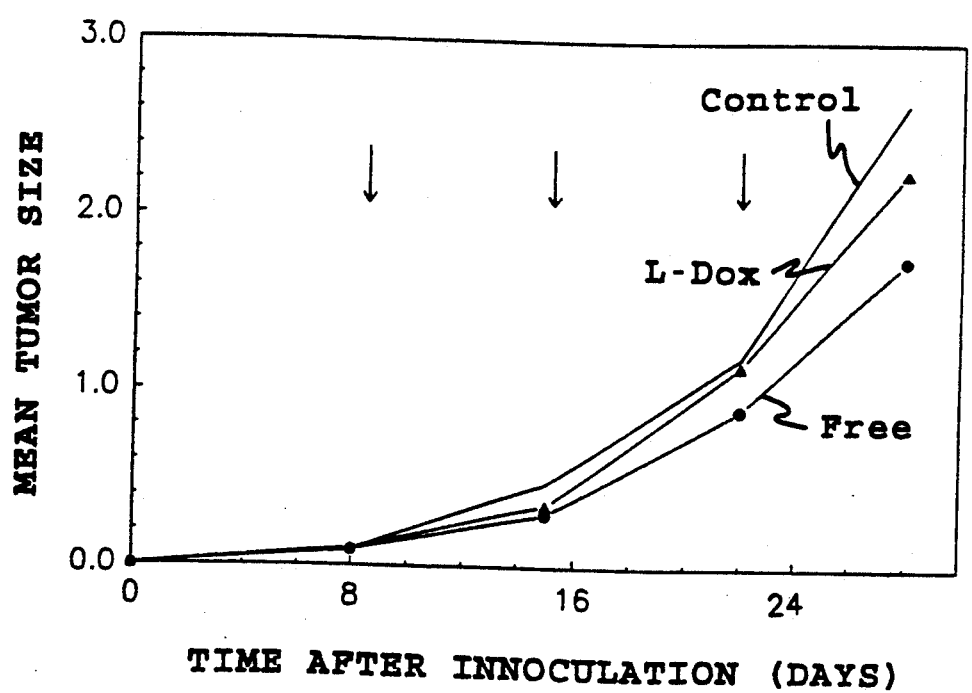
FIG. 17 is a plot similar to that in FIG. 15, showing tumor size growth, in days following subcutaneous implantation of a C-26 colon carcinoma, for animals treated with a saline control (filled circles), or animals treated with 10 mg/kg doxorubicin in free form (filled squares), or in conventional liposomes (open circles)
Figure 18A:
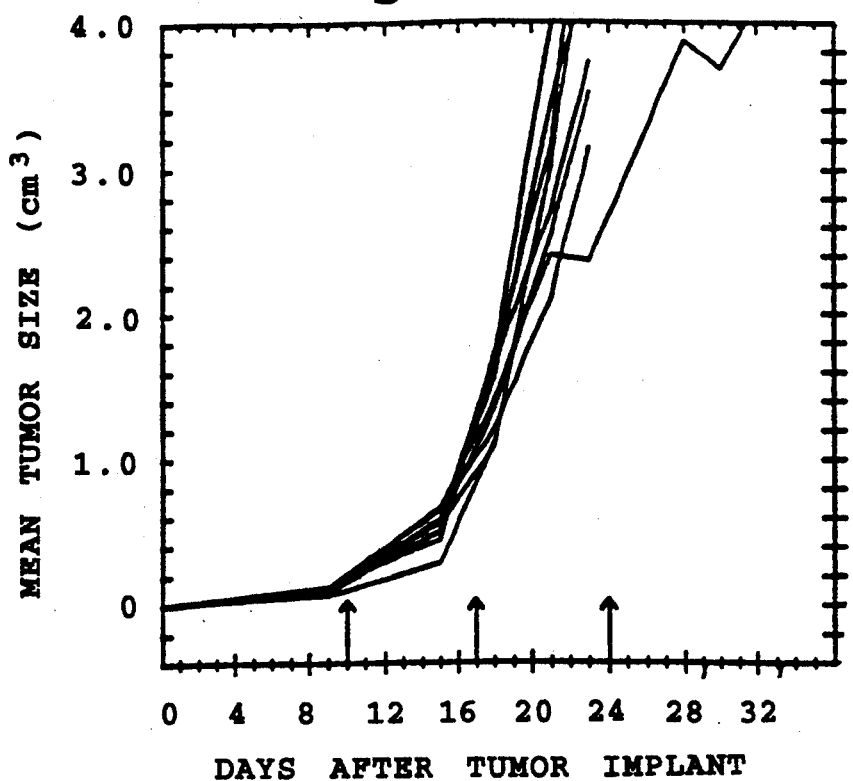
FIG. 18 shows plots of tumor size as a function of time following tumor implantation in animals, each treated with (A) (a) saline control, (B) 6 mg/kg free epirubicin, (C) PEG liposomes at 6 mg/kg, (D) PEG liposomes at 9 mg/kg, or (E) empty liposomes mixed with free epirubicin at 6 mg/kg in individual animals (10 animals per group), where (F) shows mean values for all five treatment groups for saline (open diamonds), free epirubicin, 6 mg/kg (filled circles), mixture of free drug and empty liposomes (open circles), and PEG liposomes with entrapped epirubicin at 6/mg/kg (filled triangles) and 9 mg/kg (open squares)
Figure 18B:
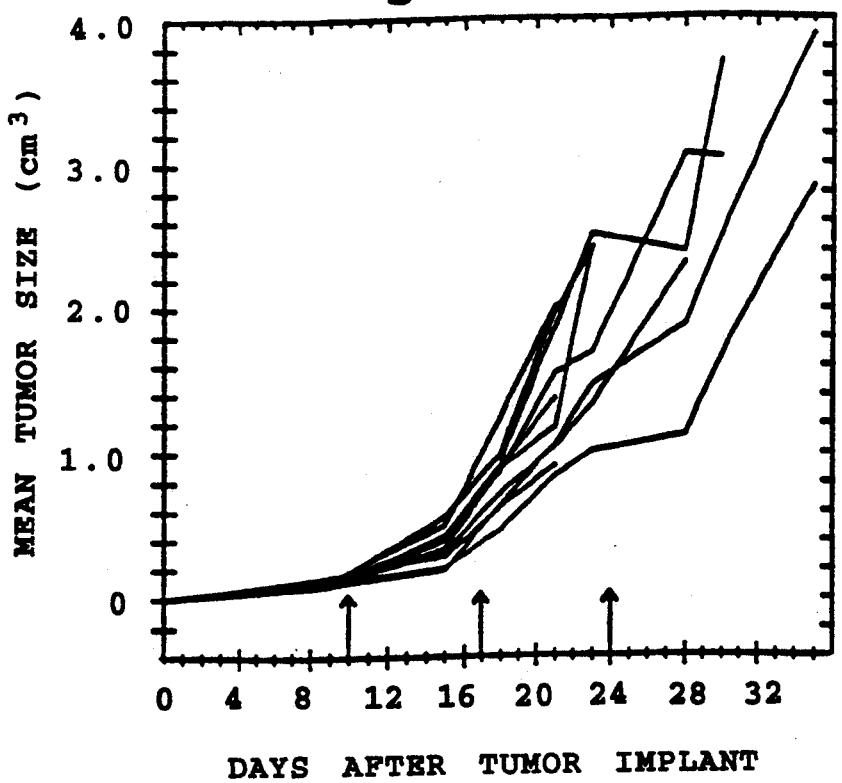
Figure 18C:
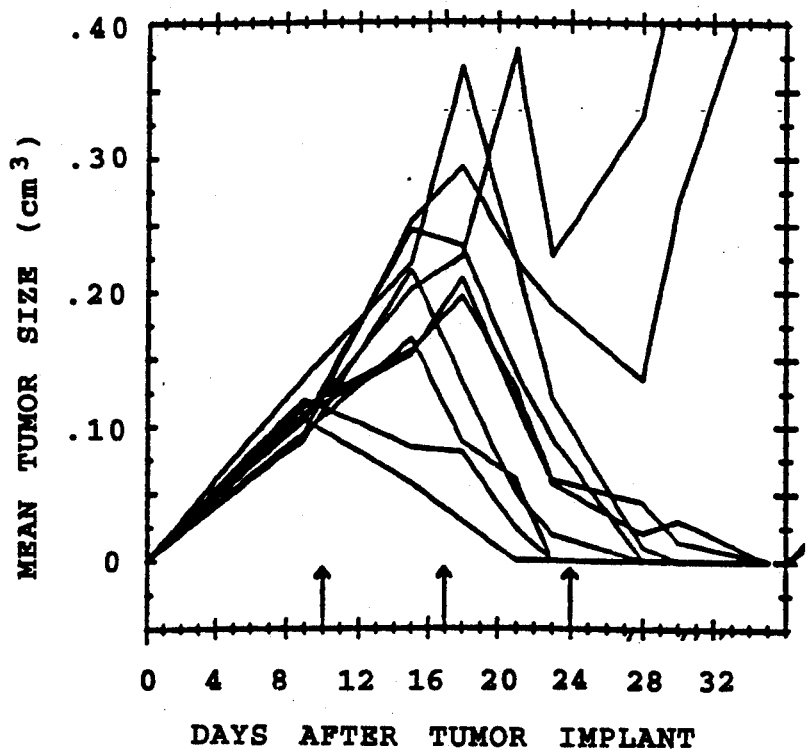
Figure 18D:
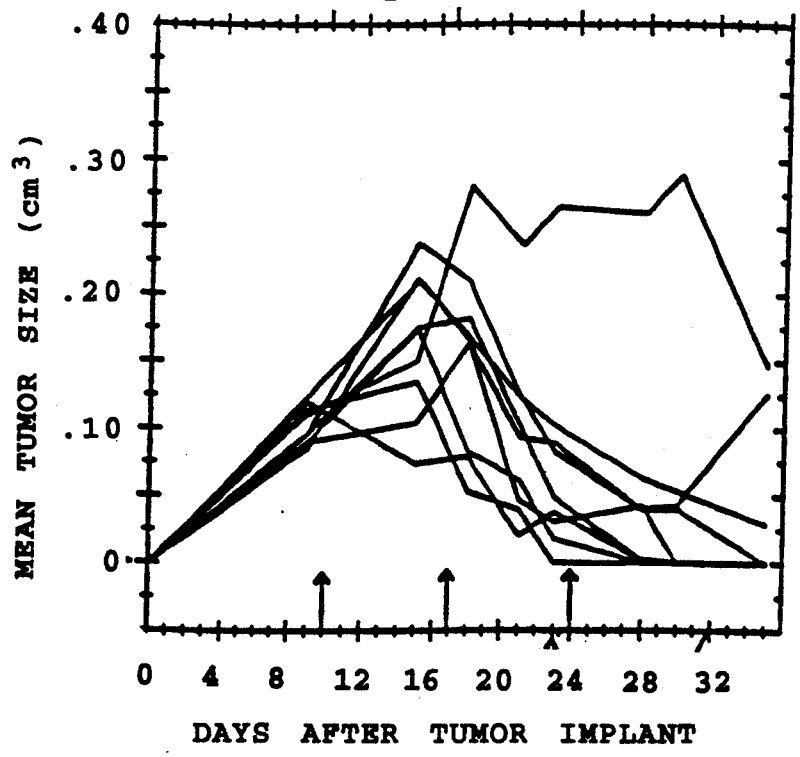
Figure 18E:
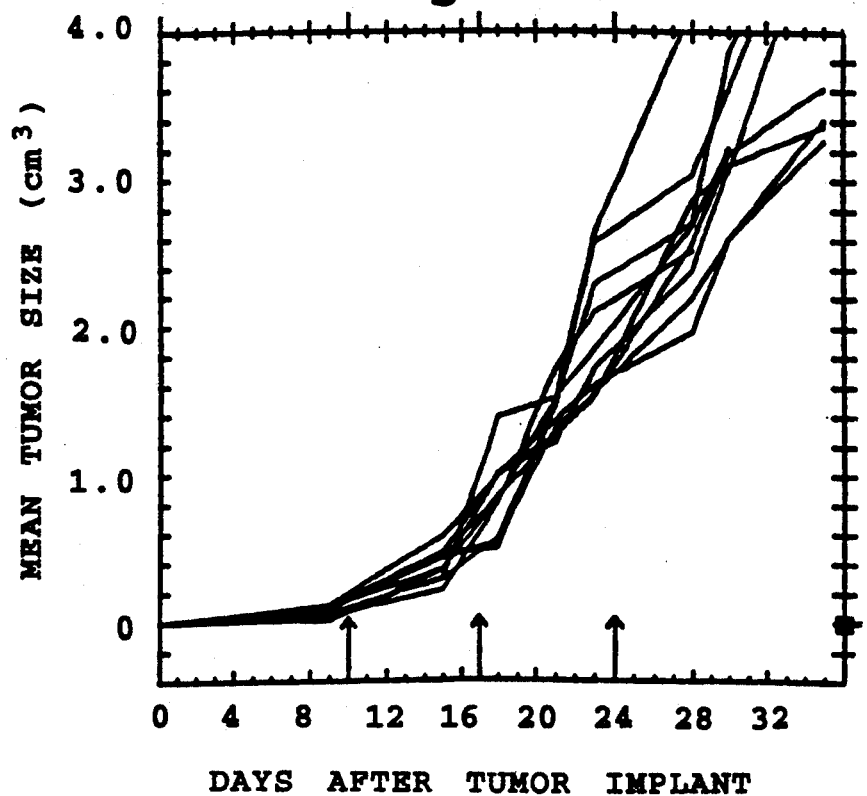
Figure 18F:
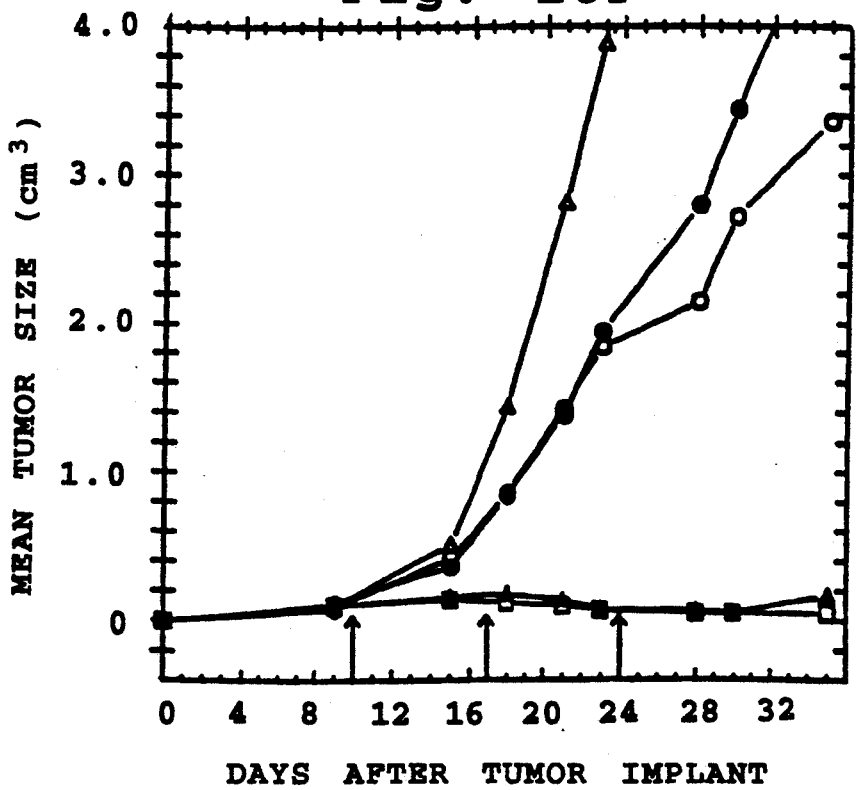

Although reduced toxicity may contribute to the increased efficacy of tumor treatment reported above, selective localization of the drug by liposomal extravasation is also important for improved drug efficacy. This is demonstrated in the drug treatment method described in Example 18. Here conventional liposomes containing doxorubicin (which show little or no tumor uptake by extravasation when administered IV) were compared with free drug at the same dose (10 mg/kg) to reduce the rate of growth of a subcutaneously implanted tumor. FIG. 17 plots tumor size with time in days following tumor implantation for a saline control (solid line), free drug (filled circles) and conventional liposomes (filled triangles). As seen conventional liposomes do not suppress tumor growth to any greater extent than free drug at the same dose. This finding stands in stark contrast to the results shown in FIGS. 15A-C and 16 where improved survival and tumor growth suppression is seen compared to free drug when tumor-bearing animals are treated with anthracyclines anti-tumor drugs entrapped in PEG liposomes.

Thus, the tumor-treatment method allows both higher levels of drug to be administered, due to reduced drug toxicity in liposomes, and greater drug efficacy, due to selective liposome localization in the intercellular fluid of the tumor.

It will be appreciated that the ability to localize a compound selectively in a tumor, by liposome extravasation, can also be exploited for improved targeting of an imaging agent to a tumor, for tumor diagnosis. Here the imaging agent, typically a radioisotope in chelated form, or a paramagnetic molecule, is entrapped in liposomes, which are then administered IV to the subject being examined. After a selected period, typically 24-48 hours, the subject is then monitored, for example by gamma scintillation radiography in the case of the radioisotope, or by nuclear magnetic resonance (NMR) in the case of the paramagnetic agent, to detect regions of local uptake of the imaging agent.

It is also anticipated that long circulating polymer-containing liposomes would be useful for delivery of anti-infective drugs to regions of infections. Sites of infection, like tumors, often exhibit compromised leaky endothelial barriers—as evidenced by the fact that edema (fluid uptake from the bloodstream) is quite often found at these sites. It is expected that PEG liposomes containing antibiotics (such as aminoglycosides, cephalosporins, and beta lactams) would improve drug localization at sites of infection, thereby improving the therapeutic index of such agents—particularly ones which exhibit dose-related toxicities, such as the aminoglycosides.

The following examples illustrate methods of preparing liposomes with enhanced circulation times, and for accessing circulation times in vivo and in vitro. The examples are intended to illustrate specific liposome compositions and methods of the invention, but are in no way intended to limit the scope thereof.

MATERIALS

Cholesterol (Chol) was obtained from Sigma (St. Louis, Mo.). Sphingomyelin (SM), egg phosphatidylcholine (lecithin or PC), partially hydrogenated PC having the composition IV40, IV30, IV20, IV10, and IV1, phosphatidylglycerol (PG), phosphatidylethanolamine (PE), dipalmitoyl-phosphatidyl glycerol (DPPG), dipalmitoyl PC (DPPC), dioleyl PC (DOPC) and distearoyl PC (DSPC) were obtained from Avanti Polar Lipids (Birmingham, AL) or Austin Chemical Company (Chicago, Ill.). [$^{125}$I]-tyraminyl-inulin was made according to published procedures. $^{67}$Gallium-citrate was supplied by NEN Neoscan (Boston, Mass.). Doxorubicin HCl and Epirubicin HCL were obtained from Adria Laboratories (Columbus. Ohio) or Farmitalia Carlo Erba (Milan, Italy).

EXAMPLE 1

Preparation of PEG-PE Linked by Cyanuric Chloride

A. Preparation of activated PEG 2-0-Methoxypolyethyleneglycol 1900-4,6-dichloro-1,3,5 triazine previously called activated PEG was prepared as described in J. Biol. Chem., 252:3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature. The solution was filtered, and 600 ml of petroleum ether (boiling range, 35-60°) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector. Titration of activated PEG-1900 with silver nitrate after overnight hydrolysis in aqueous buffer at pH 10.0, room temperature, gave a value of 1.7 mol of chloride liberated/mol of PEG.

TLC analysis of the product was effected with TLC reversed-phase plates obtained from Baker using methanol/water, 4:1; v/v, as developer and exposure to iodine vapor for visualization. Under these conditions, the starting methoxy polyglycol 1900 appeared at $R_f=0.54$ to 0.60. The activated PEG appeared at $R_f=0.41$. Unreacted cyanuric chloride appeared at $R_f=0.88$ and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyglycol 1900)-1,3,5-triazinyl egg phosphatidylethanolamine.

In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained. This solid was dissolved in 5 ml of a mixture of 4 volumes of acetone and 1 volume of acetic acid. The resulting mixture was placed at the top of a 21 mm×240 mm chromatographic absorption column packed with silica gel (Merck Kieselgel 60, 70-230 mesh) which had first been moistened with a solvent composed of acetone acetic acid, 80/20; v/v.

The column chromatography was developed with the same solvent mixture, and separate 20 to 50 ml aliquots of effluent were collected. Each portion of effluent was assayed by TLC on silica gel coated plates, using 2-butanone/acetic acid/water; 40/25/5; v/v/v as developer and iodine vapor exposure for visualization. Fractions containing only material of $R_f$=about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/chloroform; 50/50 chloroform and centrifuged to remove insoluble material. Evaporation of the clarified solution to dryness under vacuum afforded 21 mg (7.62 micromoles) of colorless solid.

EXAMPLE 2

Preparation of Carbamate and Amide Linked Hydrophilic Polymers with PE

A. Preparation of the imidazole carbamate of polyethylene glycol methyl ether 1900.

9.5 grams (5 mmoles) of polyethylene glycol methyl ether 1900 obtained from Aldrich Chemical Co. was dissolved in 45 ml benzene which has been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and the clear solution formed at room temperature. The solution was diluted to 50.0 ml with dry benzene and stored in the refrigerator as a 100 micromole/ml stock solution of the imidazole carbamate of PEG ether 1900.

B. Preparation of the phosphatidylethanolamine carbamate of polyethylene glycol methyl ether 1900

10.0 ml (1mmol) of the 100 mmol/ml stock solution of the imidazole carbamate of polyethylene glycol methyl ether 1900 was pipetted into a 10 ml pear-shaped flask. The solvent was removed under vacuum. 3.7 ml of a 100 mg/ml solution of egg phosphatidyl ethanolamine in chloroform (0.5 mmol) was added. The solvent was evaporated under vacuum. 2 ml of 1,1,2,2-tetrachloroethylene and 139 microliters (1.0 mmol) of triethylamine VI was added. The vessel was Closed and heated in a sand bath maintained at 95° C. for 6 hours. At this time, thin-layer chromatography was performed with fractions of the above mixture to determine an extent of conjugation on SiO2 coated TLC plates, using butanone/acetic acid/water; 40/5/5; v/v/v; was performed as developer. Iodine vapor visualization revealed that most of the free phosphatidyl ethanolamine of Rf=0.68, had reacted, and was replaced by a phosphorous-containing lipid at $R_f$=0.78 to 0.80.

The solvent from the remaining reaction mixture was evaporated under vacuum. The residue was taken up in 10 ml methylene chloride and placed at the top of a 21 mm×270 mm chromatographic absorption column packed with Merck Kieselgel 60 (70–230 mesh silica gel), which has been first rinsed with methylene chloride. The mixture was passed through the column, in sequence, using the following solvents.

TABLE 1

| ml | Volume % of Methylene Chloride | Volume % Methanol With 2% Acetic Acid |
|---|---|---|
| 100 | 100% | 0% |
| 200 | 95% | 5% |

TABLE 1-continued

| ml | Volume % of Methylene Chloride | Volume % Methanol With 2% Acetic Acid |
|---|---|---|
| 200 | 90% | 10% |
| 200 | 85% | 15% |
| 200 | 60% | 40% |

50 ml portions of effluent were collected and each portion was assayed by TLC on SiO2 - coated plates, using 12 vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of colorless wax of phosphatidyl etha-nolamine carbamate of polyethylene glycol methyl ether. This represented 263 micromoles and a yield of 52.6% based on the phosphatidyl ethanolamine. An NMR spectrum of the product dissolved in deuterochloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidyethanolamine carbamate, M.W. 2,654.

C. Preparation of polylactic acid amide of phosphotidyletanolamine 200 mg (0.1 mmoles) poly (lactic acid), m. wt.=2,000 (ICN, Cleveland, Ohio) was dissolved in 2.0 ml dimethyl sulfoxide by heating while stirring to dissolve the material completely. Then the solution was cooled immediately to 65° C. and poured onto a mixture of 75 mg (0.1 mmoles) of distearylphosphatidyl-ethanolamine (Cal. Biochem, La Jolla) and 41 mg (0.2 mmoles) dicyclohexylcarbodiimide. Then 28 ml (0.2 mmoles) of triethylamine was added, the air swept out of the tube with nitrogen gas, the tube capped, and heated at 65° C. for 48 hours.

After this time, the tube was cooled to room temperature, and 6 ml of chloroform added. The chloroform solution was washed with three successive 6 ml volumes of water, centrifuged after each wash, and the phases separated with a Pasteur pipette. The remaining chloroform phase was filtered with suction to remove suspended distearolyphosphatidyl ethanolamine. The filtrate was dried under vacuum to obtain 212 mg of semi-crystalline solid.

This solid was dissolved in 15 ml of a mixture of 4 volumes ethanol with 1 volume water and passed through a 50 mm deep and 21 mm diameter bed of H. Dowex 50 cation exchange resin, and washed with 100 ml of the same solvent.

The filtrate was evaporated to dryness to obtain 131 mg colorless wax.

291 mg of such wax was dissolved in 2.5 ml chloroform and transferred to the top of a 21 mm × 280 mm column of silica gel wetted with chloroform. The chromatogram was developed by passing through the column, in sequence, 100 ml each of:

100% chloroform, 0% (1% NH4OH in methanol);
90% chloroform, 10% (1% NH4OH in methanol);

85% chloroform, 15% (1% NH₄OH in methanol);
80% chloroform, 20% (1% NH₄OH in methanol);
70% chloroform, 30% (1% NH₄OH in methanol);

Individual 25 ml portions of effluent were saved and assayed by TLC on SFO₂-coated plates, using CHCl₃, CH₃OH, H₂O, con. NH₄OH, 130, 70, 8, 0.5 v/v as developer and I₂, vapor absorption for visualization. The 275–325 ml portions of column effluent contained a single material, PO₄+, of $R_f$=0.89.

When combined and evaporated to dryness, these afforded 319 mg colorless wax.

Phosphate analysis agrees with a molecular weight of possibly 115,000.

Apparently, the polymerization of the poly (lactic acid) occurred at a rate comparable to that at which it reacted with phosphatidylethanolamine.

This side-reaction could probably be minimized by working with more dilute solutions of the reactants.

D. Preparation of polyglycolic acid amide of DSPE

A mixture of 266 mg. (3.50 mmoles) glycolic acid, 745 mg (3.60 mmoles) dicyclohexyl carbodiimide, 75 mg. (0.10 mmoles) distearoyl phosphatidyl ethanolamine, 32 microliters (0.23 mmoles triethyl amine, and 5.0 ml dry dimethyl sulfoxide was heated at 75° C., under a nitrogen atmosphere, cooled to room temperature, then diluted with an equal volume of chloroform, and then washed with three successive equal volumes of water to remove dimethyl sulfoxide. Centrifuge and separate phases with a Pasteur pipette each time.

Filter the chloroform phase with suction to remove a small amount of suspended material and vacuum evaporate the filtrate to dryness to obtain 572 mg. pale amber wax.

Re-dissolve this material in 2.5 ml chloroform and transfer to the top of a 21 mm × 270 mm column of silica gel (Merck Hieselgel 60) which has been wetted with chloroform.

Develop the chromatogram by passing through the column, in sequence, 100 ml each of:
100% chloroform, 0% (1% NH₄OH in methanol);
90% chloroform, 10% (1% NH₄OH in methanol);
85% chloroform, 15% (1% NH₄OH in methanol);
80% chloroform, 20% (1% NH₄OH in methanol);
70% chloroform, 30% (1% NH₄OH in methanol).

Collect individual 25 ml portions of effluent and assay each by TLC on Si)₂-coated plates, using CH Cl₃, CH₃OH, H₂O, con-NH₄OH; 130, 70, 8, 0.5 v/v as developer.

Almost all the P04 + material will be in the 275–300 ml portion of effluent. Evaporation of this to dryness under vacuum, followed by high-vacuum drying, affords 281 mg of colorless wax.

Phosphate analysis suggests a molecular weight of 924,000.

Manipulation of solvent volume during reaction and molar ratios of glycolic acid and dicyclohexyl carbodiimide would probably result in other sized molecules.

E. Preparation of Polyglycolic/Polylactic acid amide of PE.

The same synthetic approach detailed above can be applied to the preparation of random polylactic/polyglycolic copolymers chemically linked to PE by an amide bond. In this case, equimolar quantities of distearoyl phosphatidyl ethanolamine and a 1-to-1 mixture of polyglycolic acid, polylactic acid are mixed with a three-fold molar excess of dicyclohexyl carbodiimide and a two-fold molar excess of triethylamine in a sufficient volume of dimethyl sulfoxide to dissolve all components at 75° C. The reaction is allowed to proceed 48 hours under an inert atmosphere. The product is purified by column chromatography as described above for the polylactic and polyglycolic amides of PE.

EXAMPLE 3

Preparation of Ethylene-Linked PEG-PE

A. Preparation of I-trimethylsilyloxy-polyethylene glycol is illustrated in the reaction scheme shown in FIG. 4.

15.0 gm (10 mmoles) of polyethylene glycol) M.Wt. 1500, (Aldrich Chemical) was dissolved in 80 ml benzene. 1.40 ml (11 mmoles) of chlorotrimethyl silane (Aldrich Chemical Co.) and 1.53 ml (lmmoles) of triethylamine was added. The mixture was stirred at room temperature under an inert atmosphere for 5 hours.

The mixture was filtered with suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si—C₁₈ reversed-phase plates using a mixture of 4 volumes of ethanol with 1 volume of water as developer, and iodine vapor visualization, revealed that all the polyglycol 1500 ($R_f$=0.93) has been consumed, and was replaced by a material of $R_f$=0.82. An infra-red spectrum revealed absorption peaks characteristic only of polyglycols.

Yield of I-trimethylsilyoxypolyethylene glycol, M.W. 1500 was nearly quantitative.

B. Preparation of trifluoromethane sulfonyl ester of ltrimethylsilyloxy-polyethylene glycol 15.74 grams (10 mmol) of the crystalline I-trimethylsilyloxy polyethylene glycol obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy polyethylene glycol was done.

C. Preparation of N-1-trimethylsilyloxy polyethylene glycol 1500 PE 10 ml of the methylene chloride stock solution of the trifluoromethane sulfonyl ester of 1-trimethylsilyloxy polyethylene glycol was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and the solvent was evaporated under vacuum. To the obtained residue, 5 ml dry dimethyl formamide and 70 microliters (0.50 mmoles) triethylamine (VI) was added. Air from the reaction vessel was displaced with nitrogen. The vessel was closed and heated in a sand bath a 110° C. for 22 hours. The solvent was evaporated under vacuum to obtain 1.58 grams of brownish colored oil.

A 21×260 mm chromatographic absorption column filled with Kieselgel 60 silica 70-230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyloxy polyethylene glycol 1500 PE appeared at $R_f=0.78$. Unchanged PE appeared at $R_f=0.68$.

The desired N-1-trimethylsilyloxy polyethylene glycol 1500 PE was a chief constituent of the 170-300 ml portions of column effluent. When evaporated to dryness under vacuum these portions afforded 111 mg of pale yellow oil of compound.

D. Preparation of N-polyethylene glycyl 1500: phosphatidyl-ethanolamine acetic acid deprotection Once-chromatographed, PE compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si-C18 reversed-phase plates, developed with a mixture of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm × 250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of Rf=0.08 to 0.15 were combined. This was typically the 20-100 ml portion of effluent. When evaporated to dryness, under vacuum, these portions afforded 33 mg of colorless wax PEG-PE corresponding to a yield of only 3%, based on the starting phosphatidyl ethanolamine. NMR analysis indicated that the product incorporated both PE residues and polyethylene glycol residues, but that in spite of the favorable-appearing elemental analysis, the chain length of the polyglycol chain has been reduced to about three to four ethylene oxide residues. The product prepared was used for a preparation of PEG-PE liposomes.

E. Preparation of N-Polyethylene glycol 1500 P.E. by fluoride deprotection 500 mg of crude N-1-trimethylsilyloxy polyethylene glycol PE was dissolved in 5 ml tetrahydrofuran and 189 mg (0.600 millimoles) of tetrabutyl ammonium fluoride was added and agitated until dissolved. The reactants were let to stand over night at room temperature (20° C.).

The solvent was evaporated under reduced pressure and the residue was dissolved in 10 ml chloroform, washed with two successive 10 ml portions of water, and centrifuged to separate chloroform and water phases. The chloroform phase was evaporated under vacuum to obtain mg of orange-brown wax, which was determined to be impure N-polyethylene glycol 1500 PE compound.

The wax was re-dissolved in 5 ml chloroform and transferred to the top of a 21×270 mm column of silica gel moistened with chloroform. The column was developed by passing 100 ml of solvent through the column. The Table 2 solvents were used in sequence:

TABLE 2

| Volume % Chloroform | Volume % Methanol Containing 2% Conc. Ammonium Hydroxide/methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Separated 50 ml fractions of column effluent were saved. The fractions of the column were separated by TLC on Si-C18 reversed-phase plates. TLC plates were developed with 4 volumes of ethanol mixed with 1 volume of water. Visualization was done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M.W. 2226. The proton NMR spectrum of this material dissolved in deuterochloroform showed the expected peaks due to the phosphatidyl ethanolamine portion of the molecule, together with a few methylene protons attributable to polyethylene glycol. (Delta=3.7).

EXAMPLE 4

Preparation of REVs and MLVs

A. Sized REVs

A total of 15 μmoles of the selected lipid components, in the mole ratios indicated in the examples below, were dissolved in chloroform and dried as a thin film by rotary evaporation. This lipid film was dissolved in 1 ml of diethyl ether washed with distilled water. To this lipid solution was added 0.34 ml of an aqueous buffer solution containing 5 mM Tris, 100 mM NaCl, 0.1 mM EDTA, pH 7.4, and the mixture was emulsified by sonication for 1 minute, maintaining the temperature of the solution at or below room temperature. Where the liposomes were prepared to contain encapsulated [$^{125}$I] tyraminyl-inulin, such was included in the phosphate buffer at a concentration of about 4 μCi/ml buffer. The ether solvent was removed under reduced pressure at room temperature, and the resulting gel was taken up in 0.1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.4 microns or 0.2 microns. Liposomes extruded through the 0.4 micron filter averaged 0.17± (0.05) micron diameters, and through the 0.2 micron filter, 0.16 (0.05) micron diameters. Non-encapsulated [$^{125}$I] tyraminyl-inulin was removed by passing the extruded liposomes through Sephadex G-50 (Pharmacia).

B. Sized MLVs

Multilamellar vesicle (MLV) liposomes were prepared according to standard procedures by dissolving a mixture of lipids in an organic solvent containing primarily CHCl$_3$ and drying the lipids as a thin film by rotation under reduced pressure. In some cases a radioactive label for the lipid phase was added to the lipid solution before drying. The lipid film was hydrated by addition of the desired aqueous phase and 3 mm glass beads followed by agitation with a vortex and shaking above the phase transition temperature of the phospholipid component for at least 1 hour. In some cases a radioactive label for the aqueous phase was included in the buffer. In some cases the hydrated lipid was repeatedly frozen and thawed three times to provide for ease of the following extrusion step.

The size of the liposome samples was controlled by extrusion through defined pore polycarbonate filters using pressurized nitrogen gas. In one procedure, the liposomes were extruded one time through a filter with pores of 0.4 μm and then ten times through a filter with pores of 0.1 μm. In another procedure, the liposomes were extruded three times through a filter with 0.2 μm pores followed by repeated extrusion with 0.05 μm pores until the mean diameter of the particles was below 100 nm as determined by DLS. Unencapsulated aqueous components were removed by passing the extruded sample through a gel permeation column separating the liposomes in the void volume from the small molecules in the included volume.

C. Loading $^{67}$Ga-DF Into Liposomes

The protocol for preparation of Ga$^{67}$-DF labeled liposomes as adapted from known procedures (Gabizon, 1988–1989). Briefly, REV or MLV liposomes were prepared as described above except no $^{125}$I tyraminyl-inulin was included. Rather, the ion chelator desferal mesylate (DF) was encapsulated in the internal aqueous phase and used to irreversibly trap $^{67}$Ga-DF in the liposome.

D. Dynamic Light Scattering

Liposome particle size distribution measurements were obtained by DLS using a NICOMP Model 200 with a Brookhaven Instruments BI-2030AT autocorrelator attached. The instruments were operated according to the manufacturer's instructions. The NICOMP results were expressed as the mean diameter and standard deviation of a Gaussian distribution of vesicles by relative volume.

EXAMPLE 5

Liposome Blood Lifetime Measurements

A. Measuring Blood Circulation Time and Blood/RES Ratios

In vivo studies of liposomes were performed in two different animal models: Swiss-Webster mice at 25 g each and laboratory rats at 200–300 g each. The studies in mice involved tail vein injection of liposome samples at 1 μM phospholipid/mouse followed by animal sacrifice after a defined time and tissue removal for label quantitation in a scintillation counter. The weight and percent of the injected dose in each tissue were determined. The studies in rats involved establishment of a chronic catheter in a femoral vein for removal of blood samples at defined times after injection of liposome samples in a catheter in the other femoral artery at 3–4 μM phospholipid/rat. In general, rat studies were carried out using $^{67}$Ga-DF loaded liposomes and radioactivity was measured using a gamma counter. The percent of the injected dose remaining in the blood at several time points up to 24 hours, and in selected tissues at 24 hours, was determined.

B. Time Course of Liposome Retention in the Bloodstream

PEG-PE composed of methoxy PEG, molecular weight 1900 and 1-palmitoyl-2-oleyl-PE (POPE) was prepared as in Example 2. The PEG-POPE lipid was combined with and partially hydrogenated egg PC (PHEPC) in a lipid:lipid mole ratio of about 0.1:2, and the lipid mixture was hydrated and extruded through a 0.1 micron polycarbonate membrane, as described in Example 4, to produce MLV's with average size about 0.1 micron. The MLV lipids included a small amount of radiolabeled lipid marker $^{14}$C-cholesteryl oleate, and the encapsulated marker either $^3$H-inulin or $^{67}$Ga-DF as described in Example 4. The liposome composition was injected and the percent initial injected dose in mice was determined as described in Example 4, at 1, 2, 3, 4, and 24 after injection. The time course of loss of radiolabeled material is seen in FIG. 7 which is a plot of percent injected dose for encapsulated inulin (solid circles), inulin marker corrected to the initial injection point of 100% (open circles), and lipid marker (closed triangles), over a 24-hour period post injection. As seen, both lipid and encapsulated markers showed greater than 10% of original injected dose after 24 hours.

C. 24 Hour Blood Liposome Levels

Studies to determine percent injected dose in the blood, and blood/RES ratios of a liposomal marker, 24 hours after intravenous liposome injection, were carried out as described above. Liposome formulations having the compositions shown at the left in Table 3 below were prepared as described above. Unless otherwise noted, the lipid-derivatized PEG was PEG-1900, and the liposome size was 0.1 micron. The percent dose remaining in the blood hours after intravenous administration, and 24-hour blood/RES ratios which were measured are shown in the center and right columns in the table, respectively.

TABLE 3

| Lipid Composition* | 24 Hours After IV Dose | |
|---|---|---|
| | % Injected Dose in Blood | B/RES |
| PG:PC:Chol (.75:9.25:5) | 0.2 | 0.01 |
| PC:Chol (10:5) | 0.8 | 0.03 |
| PEG-DSPE:PC:Chol | 23.0 | 3.0 |
| PEG-DSPE:PC:Chol (250 nm) | 9.0 | 0.5 |
| PEG$_{5000}$-DSPE:PC:Chol | 21.0 | 2.2 |
| PEG$_{120}$-DSPE:PC:Chol | 5.0 | 2.0 |
| PEG-DSPE:PC (0.75:9.25) | 22.0 | 0.2 |
| PEG-DSPE:PG:PC:Chol (0.75:2.25:7:5) | 40.0 | 4.0 |
| PEG-DSPE:NaCholSO$_4$:PC:Chol (0.75:0.75:9.25:4.25) | 25.0 | 2.5 |

*All formulations contain 33% cholesterol and 7.5% charged component and were 100 nm nesm diameter except as noted. PEG-DSPE consisted of PEG$_{1900}$ except as noted. Liposome distribution and kinetics were followed using encapsulated $^{67}$Ga-DF as a label. Rates were injected IV as described in Example 4.

As seen, percent dose remaining in the blood 24 hours after injection ranged between 5–40% for liposomes containing PEG-derivatized lipids. By contrast, in both liposome formulations lacking PEG-derivatized lipids, less than 1% of liposome marker remained after 24 hours. Also as seen in Table 3, blood/RES ratios increased from 0.01–0.03 in control liposomes to at least 0.2, and as high as 4.0 in liposomes containing PEG-derivatized liposomes.

C. Blood lifetime measurements with polylactic acid derivatized PE.

Figure 10:
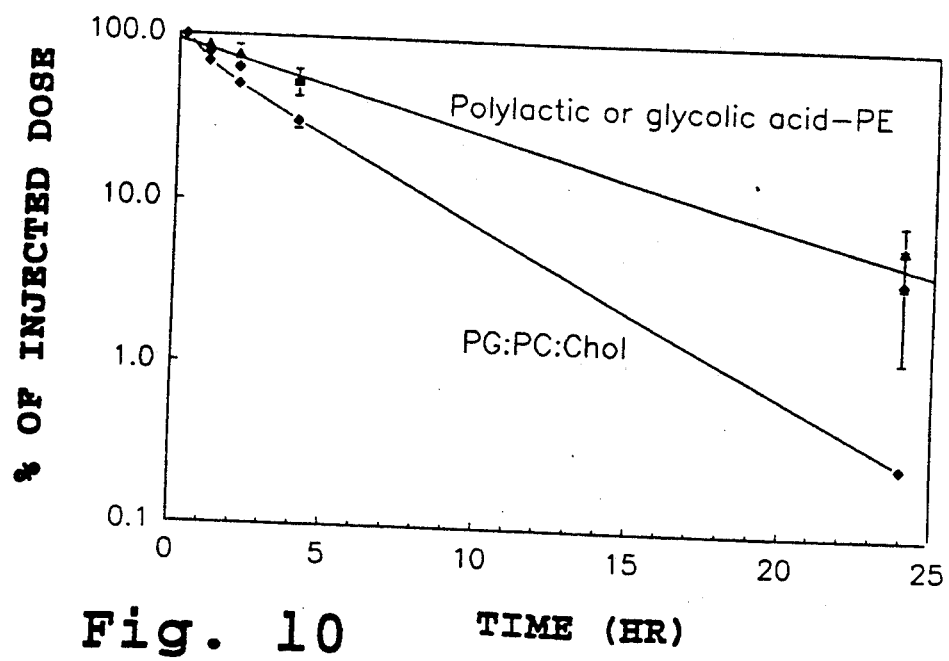
FIG. 10 is a plot similar to that of FIG. 7, showing the blood residence time of polylactic or polyglycolic acid-coated liposomes (upper lines) and conventional uncoated liposomes (lower lines)

Studies to determine percent injected dose in the blood at several times after intravenous liposome injection were carried out as described above. Typical results with extruded MLV liposome formulation having the composition Polylactic Acid-PE:HSPC:Chol at either 2:3.5:1 or 1:3.5:1 weight % is shown in FIG. 10 (solid squares). The percent dose remaining normalized at 15 min. is shown over 24 hours.

These data indicate that the clearance of the polylactic acid-coated liposomes is severalfold slower than similar formulations without polylactic acid derivatized PE.

D. Blood lifetime measurements with polyglycolic acid Derivatized PE

Studies to determine percent injected dose in the blood at several times after intravenous liposome injection were carried out as described above. Typical results with extruded MLV liposome formulation having the composition Polyglycolic Acid-PE:HSPC:Chol at 2:3.5:1 weight % are shown in FIG. 10 (open triangles). The percent dose remaining normalized at 15 min. is shown over 24 hours.

These data indicate that the clearance of the polyglycolic acid-coated liposomes is severalfold slower than similar formulations without polyglycolic acid derivatized PE.

EXAMPLE 6

Effect of Phospholipid Acyl-Chain Saturation on Blood/RES Ratios in PEG-PE Liposomes PEG-PE composed of methoxy PEG, molecular weight 1900 and distearylPE (DSPE) was prepared as in Example 2. The PEG-PE lipids were formulated with selected lipids from among sphingomyelin (SM), fully hydrogenated soy PC (PC), cholesterol (Chol), partially hydrogenated soy PC (PHSPC), and partially hydrogenated PC lipids identified as PC IV1, IV10, IV20, IV30, and IV40 in Table 4. The lipid components were mixed in the molar ratios shown at the left in Table 5, and used to form MLV's sized to 0.1 micron as described in Example 4.

TABLE 4

| Egg PC Form | Phase Transition Temperature Range °135 C. | Mole % Fatty Acid Comp. | | | | | | |
|---|---|---|---|---|---|---|---|---|
| | | 18:0 | 18:1 | 18:2 | 20:0 | 20:1-4 | 22:0 | 22:1-6 |
| Native | <0 | 12 | 30 | 15 | 0 | 3 | 0 | 5 |
| IV 40 | °0 | 14 | 32 | 4 | 0 | 3 | 0 | 4 |
| IV 30 | <20-30 | 20 | 39 | 0 | 1 | 2 | 3 | 4 |
| IV 20 | 23-45 | 30 | 10 | 0 | 2 | 1 | 3 | 3 |
| IV 10 | 37-50 | 42 | 4 | 0 | 3 | 1 | 4 | 2 |
| IV 1 | 49-54 | 56 | 0 | 0 | 5 | 0 | 6 | 0 |

TABLE 5*

| | Blood | RES | B/RES | % Remaining |
|---|---|---|---|---|
| PEG-PE:SM:PC:Chol 0.2:1:1:1 | 19.23 | 6.58 | 2.92 | 49.23 |
| PEG-PE:PHSPC:Chol 0.15:1.85:1 | 20.54 | 7.17 | 2.86 | 55.14 |
| PEG-PE:PC IV1:Chol 0.15:1.85:1 | 17.24 | 13.71 | 1.26 | 60.44 |
| PEG-PE:PC IV1:Chol (two animals) 0.15:1.85:1 | 19.16 | 10.07 | 1.90 | 61.87 |
| PEG-PE:PC IV10:Chol (two animals) 0.15:1.85:1 | 12.19 | 7.31 | 1.67 | 40.73 |
| PEG-PE:PC IV10:Chol 0.15:1.85:1 | 2.4 | 3.5 | 0.69 | 12.85** |
| PEG-PE:PC IV20:Chol 0.15:1.85:1 | 24.56 | 7.52 | 3.27 | 62.75 |

TABLE 5*-continued

| | Blood | RES | B/RES | % Remaining |
|---|---|---|---|---|
| PEG-PE:PC IV20:Chol 0.15:1.85:1 | 5.2 | 5.7 | 0.91 | 22.1** |
| PEG-PE:PC IV40:Chol 0.15:1.85:1 | 19.44 | 8.87 | 2.19 | 53.88 |
| PEG-PE:PC IV:Chol 0.15:1.85:0.5 | 20.3 | 8.8 | 2.31 | 45.5 |
| PEG-PE:EPC:Chol 0.15:1.85:1 | 15.3 | 9.6 | 1.59 | 45.9 |

*Groups of at least 3 mice were used per experiment except where otherwise noted and Ga-DF was used to follow the liposomes.
**Values with low recoveries (i.e., <40%) are considered unreliable.

24 hours after injection, the percent material injected (as measured by percent of $^{67}$Ga-DF) remaining in the blood and in the liver (L) and spleen (S) were determined, and these values are shown in the two data columns at the left in Table 5. The blood and L+S (RES) values were used to calculate a blood/RES value for each composition. The column at the right in Table 5 shows total amount of radioactivity recovered. The two low total recovery values in the table indicate anomalous clearance behavior.

The results from the table demonstrate that the blood-/RES ratios are largely independent of the fluidity, or degree of saturation of the phospholipid components forming the liposomes. In particular, there was no systematic change in blood/RES ratio observed among liposomes containing largely saturated PC components (e.g., IV1 and IV10 PC's), largely unsaturated PC components (IV40), and intermediate-saturation components (e.g., IV20).

In addition, a comparison of blood/RES ratios obtained using the relatively saturated PEG-DSPE compound and the relatively unsaturated PEG-POPE compound (Example 5) indicates that the degree of saturation of the derivatized lipid is itself not critical to the ability of the liposomes to evade uptake by the RES.

EXAMPLE 7

Effect of Cholesterol and Ethoxylated Cholesterol on Blood/RES Ratios in PEG-PE Liposomes A. Effect of added cholesterol PEG-PE composed of methoxy PEG, molecular weight 1900 and was derivatized with DSPE as described in Example 2. The PEG-PE lipids were formulated with selected lipids from among sphingomyelin (SM), fully hydrogenated soy PC (PC), and cholesterol (Chol), as indicated in the column at the left in Table 6 below. The three formulations shown in the table contain about 30, 15, and 0 mole percent cholesterol. Both REV's (0.3 micron size) and MLV's (0.1 micron size) were prepared, substantially as in Example 4, with encapsulated tritium-labeled inulin.

The percent encapsulated inulin remaining in the blood 2 and 24 hours after administration, given at the left in Table 6 below, show no measurable effect of cholesterol, in the range 0-30 mole percent.

TABLE 6

| $^3$H-Inulin | % Injected Dose In Blood | | | |
|---|---|---|---|---|
| | 2 HR. $^3$H Aqueous Label (Leakage) | 24 HR. | 2 HR. $^{14}$C - Lipid Label | 24 HR. |
| 1) SM:PC:Chol:PEG-DSPE 1: 1: 1: 0.2 | | | | |
| 100 nm MLV | 19 | 5 | 48 | |
| 300 nm REV | 23 | 15 | 67 | |
| 2) SM:PC:Chol:PEG-DSPE 1: 1: 0.5: 0.2 | 23 | 15 | 71 | |
| 300 nm REV | | | | |
| 3) SM:PC:PEG-DSPE 1: 1: 0.2 | | | | |
| 100 nm MLV | 19 | 6 | 58 | 24 |
| 300 nm REV | 32 | 23 | 76 | 43 |

B. Effect of ethoxylated cholesterol

Methoxy-ethoxy-cholesterol was prepared by coupling methoxy ethanol to cholesterol via the trifluorosulfonate coupling method described in Section I. PEG-PE composed of methoxy PEG, molecular weight 1900 and was derivatized DSPE as described in Example 2. The PEG-PE lipids were formulated with selected lipids from among distearylPC (DSPC), partially hydrogenated soy PC (HSPC), cholesterol, and ethoxylated cholesterol, as indicated at the left in Table 7. The data show that (a) ethoxylated cholesterol, in combination with PEG-PE, gives about the same degree of enhancement of liposome lifetime in the blood as PEG-PE alone. By itself, the ethoxylated cholesterol provides a moderate degree of enhancement of liposome lifetime, but substantially less than that provided by PEG-PE.

TABLE 7

| Formulation | % Injected Dose In Blood $^{14}$C-Chol-Oleate | |
|---|---|---|
| | 2 HR. | 24 HR. |
| HSPC:Chol:PEG-DSPE 1.85: 1: 0.15 | 55 | 9 |
| HSPC:Chol:PEG-DSPE:PEG$_5$-Chol 1.85: 0.85: 0.15: 0.15 | 57 | 9 |
| HSPC:Chol:HPC:PEG$_5$-Chol 1.85: 0.85: 0.15: 0.15 | 15 | 2 |
| HSPC:Chol:HPG 1.85: 1: 0.15 | 4 | 1 |

EXAMPLE 8

Effect of Charged Lipid Components on Blood/RES Ratios in PEG-PE Liposomes

PEG-PE composed of methoxy PEG, molecular weight 1900 and was derivatized DSPE as described in Example 2. The PEG-PE lipids were formulated with lipids selected from among egg PG (PG), partially hydrogenated egg PC (PHEPC), and cholesterol (Chol), as indicated in the FIG. 7. The two formulations shown in the figure contained about 4.7 mole percent (triangles) or 14 mole percent (circles) PG. The lipids were prepared as MLV's, sized to 0.1 micron as in Example 4.

The percent of injected liposome dose present 0.25, 1, 2, 4, and 24 hours after injection are plotted for both formulations in FIG. 7. As seen, the percent PG in the composition had little or no effect on liposome retention in the bloodstream. The rate of loss of encapsulated marker seen is also similar to that observed for similarly prepared liposomes containing no PG.

EXAMPLE 9

Plasma Kinetics of PEG-Coated and Uncoated Liposomes

PEG-PE composed of methoxy PEG, molecular weight 1900 and distearylPE (DSPE) was prepared as in Example 2. The PEG-PE lipids were formulated with PHEPC, and cholesterol, in a mole ratio of 0.15:1.85:1. A second lipid mixture contained the same lipids, but without PEG-PE. Liposomes were prepared from the two lipid mixtures as described in Example 5, by lipid hydration in the presence of desferal mesylate, followed by sizing to 0.1 micron, and removal of nonentrapped desferal by gel filtration with subsequent loading of $^{67}$Ga-oxine into the liposomes. The unencapsulated $^{67}$Ga was removed during passage through a Sephadex G-50 gel exclusion column. Both compositions contained 10 μmoles/ml in 0.15 M NaCl, 0.5 mM desferal.

The two liposome compositions (0.4 ml) were injected IV in animals, as described in Example 6. At time 0.25, 1, 3 or 5 and 24 hours after injection, blood samples were removed and assayed for amount inulin remaining in the blood, expressed as a percentage of the amount measured immediately after injection. The results are shown in FIG. 9. As seen, the PEG-coated liposomes have a blood halflife of about 11 hours, and nearly 30% of the injected material is present in the blood after 24 hours. By contrast, uncoated liposomes showed a halflife in the blood of less than 1 hour. At 24 hours, the amount of injected material was undetectable.

EXAMPLE 10

Preparation of Doxorubicin Liposomes

Vesicle-forming lipids containing PEG-PE, PG, PHEPC, and cholesterol, in a mole ratio of 0.15: 0.3: 1.85: 1 were dissolved in chloroform to a final lipid concentration of 25 μmol phospholipid/ml. Alpha-tocopherol (α-TC) in free base form was added in chloroform:methanol (2:1) solution to a final mole ratio of 0.5%. The lipid solution was dried to a thin lipid film, then hydrated with a warm (60° C.) solution of 125 mM ammonium sulfate containing 1 mM desferal. Hydration was carried out with 1 ml of aqueous solution per 50 μmole phospholipid. The lipid material was hydrated with 10 freeze/thaw cycles, using liquid nitrogen and a warm water bath.

Liposome sizing was performed by extrusion through two Nuclepore polycarbonate membranes, 3 cycles through 0.2 microns filters, and ten cycles through 0.05 micron filters. The final liposome size was 100 nm. The sized liposomes were then dialyzed against 50–100 volumes of 5% glucose three times during a 24 hour period. A fourth cycle was carried out against 5% glucose titered to pH 6.5–7.0 for 1 hour.

A solution of doxorubicin, 10 mg/ml in 0.9% NaCl and 1 mM desferal, was prepared and mixed with an equal volume of the dialyzed liposome preparation. The concentration of drug in the mixture was about 5 mg/ml drug 50 μmoles/ml phospholipid. The mixture was incubated for 1 hours at 60° C. in a water bath with shaking. Untrapped drug was removed by passage through a Dowex 50 WX resin packed in a small column. The column was centrifuged in a bench top centrifuge for 5 minutes to completely elute the liposome suspension. Sterilization of the mixture was by passage through a 0.45 micron membrane, and the liposomes were stored at 5° C.

EXAMPLE 11

Plasma Kinetics of Free and Liposomal Doxorubicin

PEG-PE composed of methoxy PEG, molecular weight 1900 and distearylPE (DSPE) was prepared as in Example 2. The PEG-PE lipids were formulated with hydrogenated soy bean PC (HSPC) and cholesterol, in a mole ratio of 0.15:1.85:1 (PEG-Dox). A second lipid mixture contained hydrogenated phosphatidylinositol (HPI), HSPC cholesterol, in a mole ratio of 1:10:5 (HPI-Dox). Each lipid formulation was used in preparing sized MLVs containing an ammonium ion gradient, as in Example 10.

The liposomes were loaded with doxorubicin, by mixing with an equal volume of a doxorubicin solution, 10 mg/ml plus 1 mM desferal, as in Example 15. The two compositions are indicated in FIG. 11 and Table 7 below as PEG-DOX and HPI-DOX liposomes, respectively. A doxorubicin HCl solution (the marketed product, Free Dox) was obtained from the hospital pharmacy.

Free DOX, PEG-Dox and HPI-Dox were diluted to the same concentration (1.8 mg/ml) using unbuffered 5% glucose on the day of injection. Dogs were randomized into three groups (2 females, 1 male) and weighed. An 18 gauge Venflon IV catheter was inserted in a superficial limb vein in each animal. The drug and liposome suspensions were injected by quick bolus (15 seconds). Four ml blood samples were before injection and at 5, 10, 15, 30, 45 min, 1, 2, 4, 6, 8, 10, 12, 24, 48 and 72 hours post injection. In the liposome groups blood was also drawn after 96, 120, 144, and 168 hours. Plasma was separated from the formed elements of the whole blood by centrifugation and doxorubicin concentrations assayed by standard fluorescence techniques. The amount of doxorubicin remaining in the blood was expressed as a percentage of peak concentration of labeled drug, measured immediately after injection. The results are plotted in FIG. 11, which shows that both the PEG-DOX and HPI-DOX compositions give linear logarithmic plots (single-mode exponential), and free drug give a bimodel exponential curve, as indicated in Table 8 below. The halflives of the two liposome formulations determined from these curves are indicated in Table 8.

Also shown in Table 8 is the area under the curve (AUC) determined by integrating the plasma kinetic curve over the hour test period. The AUC results indicate that the total availability of drug from PEG-DOX liposomes, for the 72 hour period following injection, was nearly twice that of HPI-DOX liposomes. This is consistent with the approximately twofold greater halflife of the PEG-DOX liposomes.

TABLE 8

|  | Free DOX | HPI-DOX | PEG-DOX |
|---|---|---|---|
| Kinetic Pattern | Bi-exp. | Mono-exp. | Mono-exp. |
| Peak Conc. (mg/l) | 0.4–2.2 | 4.3–6.0 | 4.5–5.0 |
| AUC (mg/l) | 7.1–10.0 | 73.9–97.5 | 132.9–329.9 |
| t½ hr | 1.9–3.3 | 11.1–12.0 | 19.6–45.5 |
| CL (mg/hr) | 0.6–0.9 | 1.1–1.6 | 1.3–2.2 |

EXAMPLE 12

Tissue Distribution of Doxorubicin

A. Subcutaneous Tumor

PEG-liposomes loaded with doxorubicin were prepared as in Example 10 (PEG-DOX liposomes). Free drug used was clinical material obtained from the hospital pharmacy.

Two groups of twelve mice were injected subcutaneously with $10^6$ J-6456 tumor cells. After 14 days the tumors had grown to about 1 cm$^3$ in size in the subcutaneous space and the animals were injected IV (tail vein) with 10 mg/kg doxorubicin as free drug (group 1) or encapsulated in PEG liposomes (group 2). At 4, 24, and 48 hours after drug injection, four animal in each group were sacrificed, and sections of tumor, heart, and muscle tissue were excised. Each tissue was weighed, then homogenized and extracted for determination of doxorubicin concentration using a standard florescence assay procedure Gabizon, 1989). The total drug measured in each homogenate was expressed as μg drug per gram tissue.

Figure 12B:
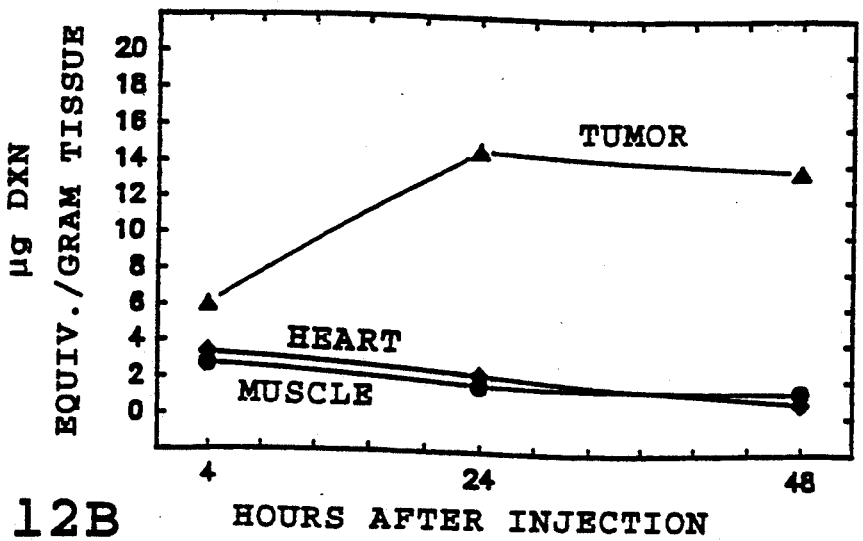

The data for drug distribution in heart, muscle, and liver are plotted in FIGS. 12A and 12B for free and liposome-associated doxorubicin, respectively. In FIG. 12A it is seen that all three tissue types take up about the same amount of drug/g tissue, although initially the drug is taken up preferentially in the heart. By contrast, when entrapped in PEG-liposomes, the drug shows a strong selective localization in the tumor, with reduced levels in heart and muscle tissue.

B. Ascites Tumor

Two groups of 15 mice were injected interperitoneally with $10^6$ J-6456 lymphoma cells. The tumor was allowed to grow for one-two weeks at which time 5 ml of ascites fluid had accumulated. The mice were then injected IV with 10 mg/kg doxorubicin either in free drug form (group 1) or entrapped in PEG liposomes as described in Example 11 (group 2). Ascites fluid was withdrawn from three animals in each group at 1, 4, 15, 24 and 48 hours post treatment. The ascites tumor was further fractionated into cellular and fluid components by centrifugation (15 min. 5000 rpm). Free and liposome-bound drug in the supernatant was determined by passing the fluid through a Dowex 50-WX-4 resin, as above, to remove free drug. The doxorubicin concentrations in the ascites fluid, tumor cells, supernatant, and resin-treated supernatant were then determined, and from these values, μg doxorubicin/gram tissue was calculated. The values for total ascites fluid supernatant (solid diamonds), supernatant after removal of free drug (solid triangles), and isolated tumor cells (solid circles) are plotted in FIG. 13. As seen, the total doxorubicin in the ascites fluid increased steadily up to about 24 hours, then dropped slightly over the next 24 hours. Most of the doxorubicin in the tumor is in liposome-entrapped form, demonstrating that liposomes are able to extravasate into solid tumors in intact form.

In a similar experiment two groups of twelve mice were implanted IP with the J-6456 llymphoma and the tumor was allowed to establish as described above. Once the ascites tumor had reached about 5 ml, one group of animals was injected with 10 mg/kg free doxorubicin and the other group with 10 mg/kg doxorubicin entrapped in PEG liposomes. At 4, 24 and 48 hours post treatment ascites fluid and blood samples were withdrawn from four animals in each group and the animals were sacrificed. Sections of liver and heart tissue were excised from each animal, homogenized and drug concentration assayed as described above. Plasma was separated from whole blood by centrifugation and drug concentration assayed as stated above. Doxorubicin concentration in the ascites fluid was also measured. The results are presented in Table 9. Plasma and ascites fluid levels are expressed as μg doxorubicin per ml and liver and heart tissue values as μg doxorubicin per gram tissue. The standard deviations for each measurement is shown in parentheses. As shown, there is considerably more doxorubicin in plasma for the group receiving the drug in PEG liposome entrapped form at all time points. Ascites tumor levels are also higher in the liposome group, particularly at the longer time points (24 and 48 hours). These data confirm the selective delivery of the drug to the tumor by the PEG liposomes.

TABLE 9

| Hours | Free | PEG-DOX | |
|---|---|---|---|
| | Plasma μg/ml (SD) | | |
| 4 | 0.9 (0.0) | 232.4 | (95.7) |
| 24 | 0.0 | 118.3 | (6.7) |
| 48 | 0.0 | 84.2 | (20.3) |
| | Ascites Tumor (tumor & fluid) μg/ml (SD) | | |
| 4 | 0.3 (0.1) | 3.8 | (2.0) |
| 24 | 0.1 (0.1) | 23.0 | (8.9) |
| 48 | 0.4 (0.3) | 29.1 | (2.0) |
| | Liver μg/gram (SD) | | |
| 4 | 8.1 (1.4) | undetectable | |
| 24 | 6.2 (4.8) | 9.8 | (5.9) |
| 48 | 6.1 (3.6) | 10.2 | (0.1) |
| | Heart μg/gram (SD) | | |
| 4 | 5.7 (3.4) | 2.4 | (0.9) |
| 24 | 2.5 (0.3) | 2.1 | (0.4) |
| 48 | 1.5 (0.6) | 2.3 | (0.1) |
| | Tumor/Heart | | |
| 4 | 0.0052 | 0.63 | |
| 24 | 0.04 | 10.9 | |
| 48 | 0.266 | 12.6 | |

EXAMPLE 13

Tumor Uptake of PEG Liposomes Compared with Conventional Liposomes

Two groups of 6 mice were injected subcutaneously with $10^5$–$10^6$ C-26 colon carcinoma cells and the tumor was allowed to grow in the subcutaneous space until it reached a size of about 1 cm$^3$ (about two weeks following injection). Each group of animals was then injected with 0.5 mg of either conventional liposomes (100 nm DSPC/Chol, 1:1) or PEG liposomes (100 nm DSPC/Chol/PEG-DSPE, 10:3:1) which had been loaded with radioactive gallium as described in Example 4. Three mice from each group were sacrificed at 2, 24 and 48 hours post treatment, the tumors excised and weighed and the amount of radioactivity quantified using a gamma counter. The results are presented in the following table and are expressed as the percent of the injected dose per gram tissue.

TABLE 10

| | PEG | | | CONVENTIONAL | | | RATIO IN TUMOR* |
|---|---|---|---|---|---|---|---|
| | Blood | Liver | Tumor | Blood | Liver | Tumor | |
| 2 hr | 38.2 | 7.2 | 3.8 | 34.1 | 11.0 | 3.7 | 1.0 |
| 24 hr | 15.1 | 14.6 | 4.2 | 7.6 | 21.6 | 3.9 | 1.1 |
| 48 hr | 5.5 | 13.8 | 3.5 | 1.2 | 25.0 | 1.7 | 2.1 |

*Expressed as amount of PEG Liposomes divided by amount of conventional liposmoes localized in the tumor As seen in Table 10, PEG liposomes are present in greater amounts in blood compared with conventional liposomes. This results in greater accumulation of PEG-containing liposomes at 48 hours as reflected in the twofold higher value of the "Ratio in Tumor" at 48 hours (right column, Table 10).

EXAMPLE 14

Liposome Extravasation into Intact Tumors: Direct Microscopic Visualization

PEG-PE composed of methoxy PEG, molecular weight 1900 and distearylPE (DSPE) was prepared as in Example 2. The PEG-PE lipids were formulated with HSPC, and cholesterol, in a mole ratio of 0.15:1.85:1. PEG-liposomes were prepared to contain colloidal gold particles (Hong). The resulting MLVs were sized by extrusion, as above, to an average 0.1 micron size. Non-entrapped material was removed by gel filtration. The final concentration of liposomes in the suspension was about 10 μmol/ml.

In a first study, a normal mouse was injected IV with 0.4 ml of the above liposome formulation. Twenty four hours after injection, the animal was sacrificed, and sections of the liver removed and fixed in a standard water-soluble plastic resin. Thick sections were cut with a microtome and the sections counterstained with a solution of silver nitrate according to instructions provided with the "Intense 2" System kit supplied by Jannsen Life Sciences, Inc. (Kingsbridge, Piscataway, N.J.), in order to intensify the staining of the colloidal gold-containing liposomes. This technique allows visualization of liposome distribution at the light microscopic level. The sections were further stained with eosin and hemotoxylin to highlight the cytoplasm and nucleus of both normal and tumor cells.

FIG. 14A is a photomicrograph of a typically liver section, showing smaller, irregularly shaped Kupfer cells, such as cells 20, among larger, more regular shaped hepatocytes, such as hepatocyes 22. The Kupfer cells show large concentrations of intact liposomes, seen as small, darkly stained bodies of the silver counterstain, such at 24 in FIG. 14A. The hepatocytes are largely free of liposomes, as would be expected.

In a second study, a C-26 colon carcinoma (about $10^6$ cell) was implanted in a mouse liver. Fourteen days post implantation, the animal was injected IV with 0.5 mg of the above liposomes. Twenty four hours later, the animal was sacrificed, and the liver was perfused, embedded, sectioned, and stained as above. The sections were examined for a capillary-fed tumor region. One exemplary region is seen in FIG. 14B, which shows a capillary 26 feeding a region of carcinoma cells, such as cells 28. These cells have characteristic staining patterns, and often include darkly stained nuclei in various stages of mitosis. The capillary in the figure is lined by an endothelial barrier 30, and just below that, a basement membrane 32.

It can be seen in FIG. 14B that liposomes, such as liposomes 34, are heavily concentrated in the tumor region, adjacent the capillary on the tumor side of the endothelial barrier and basement membrane, and many liposomes are also dispersed throughout the intercellular fluid surrounding the tumor cells.

Figure 14C:
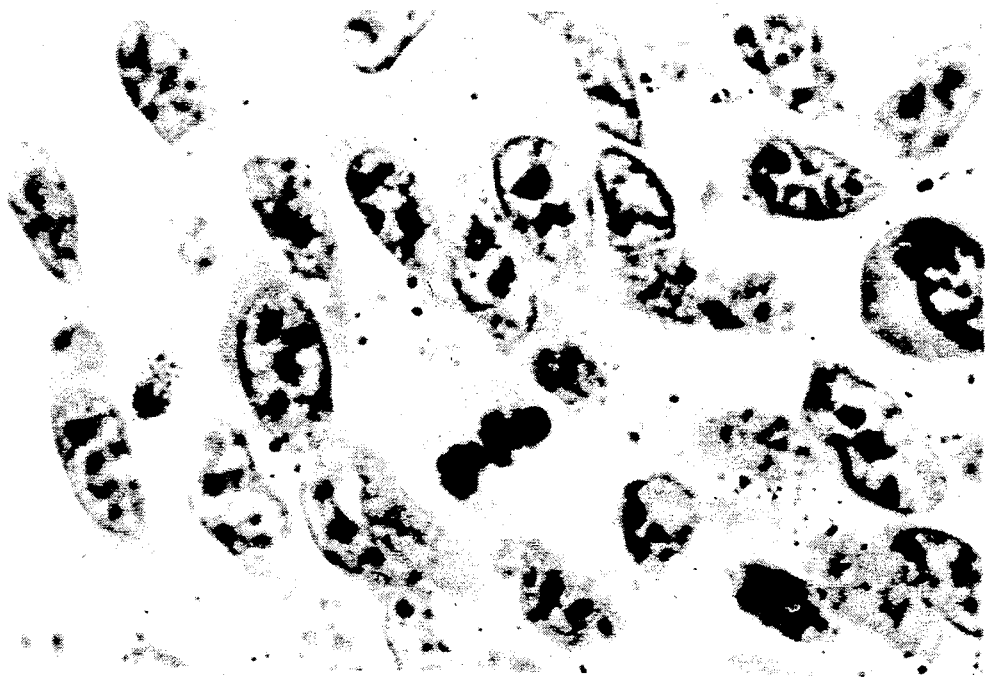
Figure 14D:
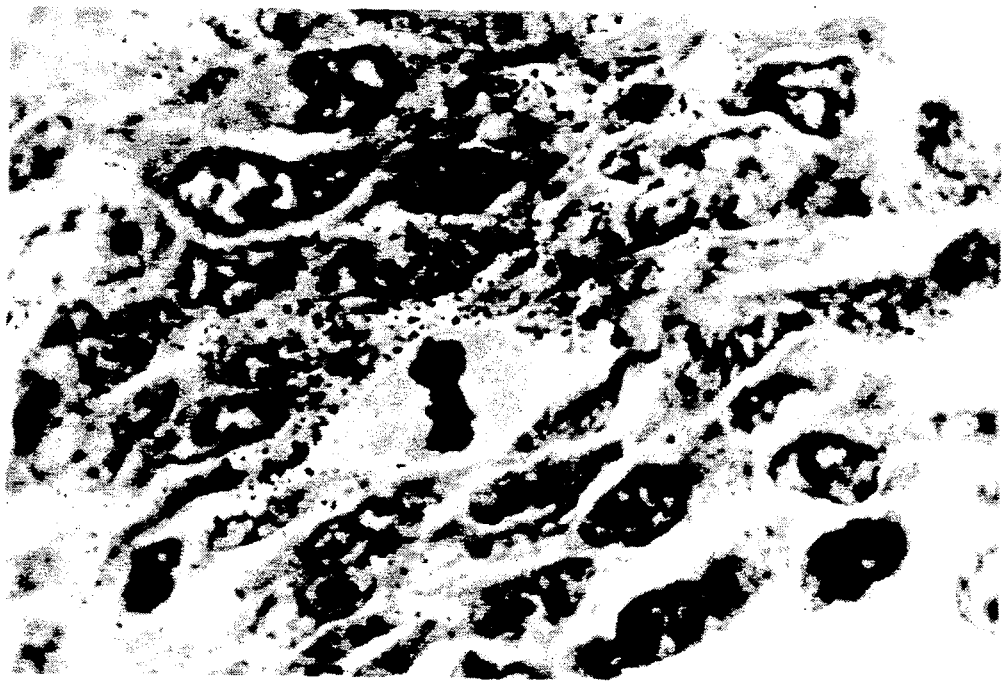

FIG. 14C shows another region of the liver tumor from the above animal. Liposomes are seen throughout the intercellular fluid bathing the carcinoma cells.

In a third study, C-26 colon carcinoma cells were injected subcutaneously into an animal, and allowed to grow in the animal for 28 days. Thereafter, the animal was injected IV with 0.5 mg of the above liposomes. Twenty four hours later, the animal was sacrificed, and the tumor mass was excised. After embedding, the tumor mass was sectioned on a microtome and stained as above. FIG. 14D shows a region of the tumor cells, including a cell 36 in the center of the figure which is undergoing abnormal mitosis typical of these tumor cells. Small, darkly stained liposomes are seen throughout the intercellular fluid.

EXAMPLE 15

Tumor Treatment Method

Vesicle-forming lipids containing PEG-PE, PG, PHEPC, and cholesterol and $\alpha$-TC in a mole ratio of 0.15: 0.3: 1.85: 1: 0.2 were dissolved in chloroform to a final lipid concentration of 25 $\mu$mol phospholipid/ml. The lipid mixture was dried into a thin film under reduced pressure. The film was hydrated with a solution of 0.125 M ammonium sulfate to form MLVs. The MLV suspension was frozen in a dry ice acetone bath and thawed three times and sized to 80–100 nm by extrusion as detailed above. An ammonium ion gradient was created substantially as described in Example 10. The liposomes were loaded with epirubicin, and free (unbound drug) removed also as described in Example 10 for doxorubicin. The final concentration of entrapped drug was about 50–100 $\mu$g drug/$\mu$mol lipid. Epirubicin HCl and doxorubicin HCL, the commercial products, were obtained from the hospital pharmacy.

A. Colon Carcinoma

About $10^6$ cells C-26 colon carcinoma cells were injected subcutaneously into three groups of 35 mice. The groups were subdivided into five 7-animal subgroups.

Figure 15A:
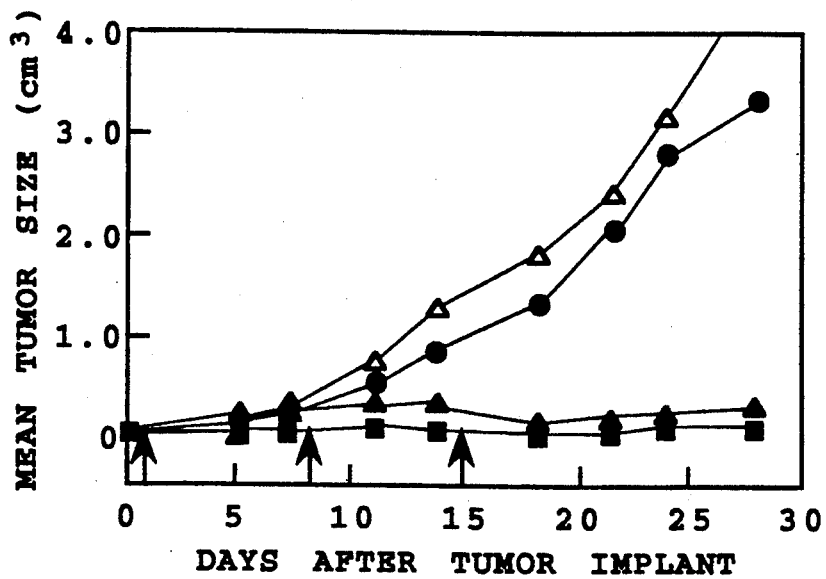
FIG. 15A-15C are plots showing tumor size growth in days following subcutaneous implantation of a C-26 colon carcinoma, for mice treated with a saline control (open circles), doxorubicin at 6 mg/kg (filled circles), epirubicin at 6 mg/kg (open triangles), or PEG-liposome-entrapped epirubicin at two doses, 6 mg/kg (filled triangles) or 12 mg/kg (open squares) on days 1, 8 and 15 (15A); for mice treated with saline (solid line), 6 mg/kg epirubicin (closed circles), 6 mg/kg epirubicin plus empty liposomes, (open circles), or PEG liposome entrapped at two doses, 6 mg/kg (filled triangles) and 9 mg/kg (open squares) on days 3, 10 and 17 (15B) or days 10, 17 and 24 (15C)

For the tumor suppression experiment shown in FIG. 15A each subgroup was injected IV with 0.5 ml of either saline vehicle control (open circles), 6 mg/kg epirubicin (open triangles), 6 mg/kg doxorubicin (filled circles), or the drug-loaded liposomes (PEG-DOX liposomes) at two doses, 6 mg/kg (filled triangles) and 12 mg/kg (open squares) on days 1, 8 and 15 following tumor cell implantation. Each group was followed for 28 days. Tumor size was measured for each animal on days 5,7,12,14,17,21,24 and 28. The growth of the tumor in each subgroup (expressed as the mean tumor size of the individual animals) at each time point is plotted in FIG. 15A.

With reference to this figure, neither free doxorubicin nor free epirubicin at 6 mg/kg significantly suppressed tumor growth compared with the saline control. In contrast, PEG liposome entrapped epirubicin both doses significantly suppresses tumor growth. With respect to survival of the animals at 120 days following tumor implantation, none of the animals in the saline, epirubicin or doxorubicin groups survived whereas 5 out of the seven and seven out of seven survived in the 6 mg/kg liposome epirubicin and 12 mg/kg liposome epirubicin groups, respectively.

Figure 15B:
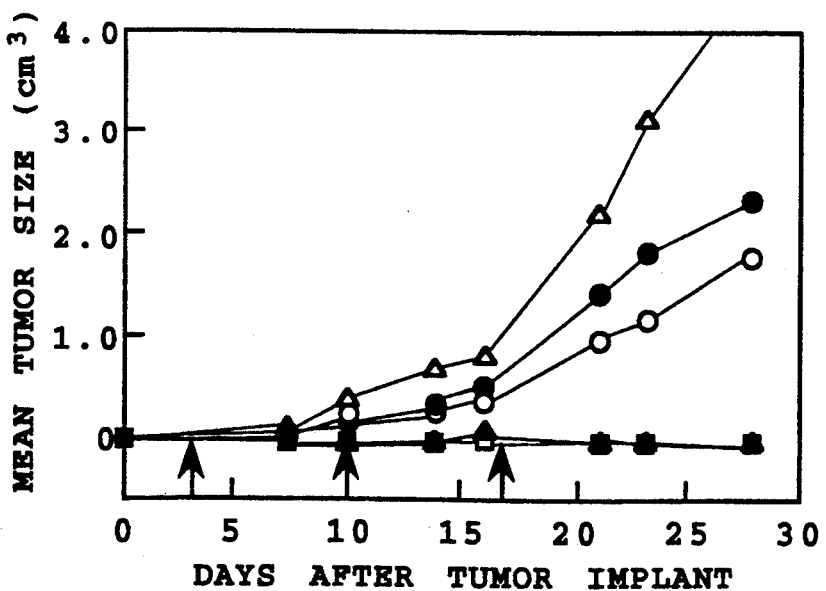
Figure 15C:
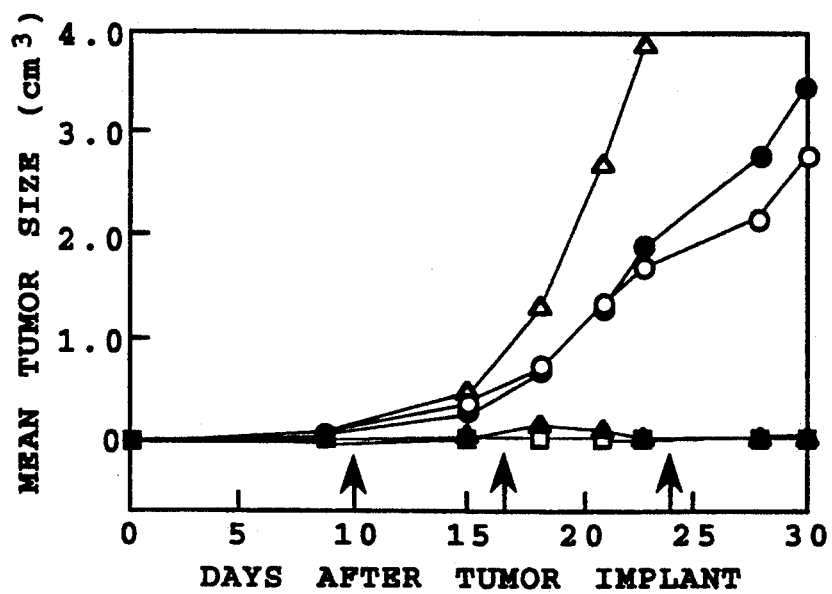

The results of delayed treatment experiments using the same tumor model are presented in FIG. 15B and 15C. The same number of animals were inoculated with the same number of tumor cells as described above. The treatment groups in FIGS. 15B and 15C consisted of saline (solid line), 6 mg/kg epirubicin (filled triangles), 6 mg/kg free epirubicin plus empty PEG liposomes (open circles) and two doses of epirubicin entrapped in PEG liposomes, 6 mg/kg (filled triangles) and 9 mg/kg (open squares). Similar to the results presented in FIG. 15A, three treatments were given in these experiments: days 3, 10 and 17 for the results plotted in FIG. 15B; and days 10, 17 and 24 for the results plotted in FIG. 15C. Significantly, in the case of the PEG liposomes with entrapped drug, both delayed treatment schedules at both dose levels resulted in tumor regression, whereas the free drug and free drug plus empty liposome treatment groups showed only a modest retardation in the rate of tumor growth.

The extent of tumor regression in the 10-day delay treatment protocol with PEG liposomes with entrapped epirubicin is illustrated in FIG. 18. The central panels of the figure (C and D) show tumor size changes in response to therapy with PEG liposomes with entrapped epirubicin injected on days 10, 17 and 24 following tumor implantation. As shown, the tumor reaches a size of about 0.20 cm$^3$ (about 200 mg) before the first treatment is administered. A tumor of 100–200 mg in a mouse is equivalent to a tumor the size of a tennis ball in a human. This "delayed treatment" protocol is considered relevant to the usual clinical situation in which tumors may be quite large before they are detected by cancer patients or their physicians.

Significantly, no tumor regression was seen with treatment by free drug (panel B) or a mixture of empty liposomes and free drug (E). In fact, it is well known that although the C-26 colon carcinoma is sensitive to epirubicin treatment in vitro, i.e., when tumor cells are bathed with a solution of the drug, the tumor fails to respond to the free drug in vivo at the highest doses and most frequent dosing intervals that can be safely set.

The observation that a fairly large C-26 tumor regresses with treatment by PEG liposomes with entrapped epirubicin treatment is thus unexpected, and indicates that PEG-liposome delivery overcomes unfavorable biodistribution and kinetics of the free drug in vivo and restores the intrinsic anti-tumor activity of this drug.

B. Breast Carcinoma

The treatment method used in part A above was employed in treating a mouse mammary carcinoma. As with the C-26 colon carcinoma cells, syngeneic mammary carcinoma cells (MC2) are sensitive in vitro to both doxorubicin and epirubicin, but when implanted subcutaneously in mice, the tumors do not respond to either agent, even at the highest doses and most aggressive dosing schedules that the animals can tolerate.

Ten-week-old female C3H/He mice were randomized into three groups of 20 animals and each received bilateral subcutaneous implants of $10^5$–$10^6$ syngeneic MC2 mouse mammary carcinoma cells on day 0. Intravenous injections of 6 mg/kg of free epirubicin, PEG liposomes with entrapped epirubicin (6 mg/kg) or a saline control were given on days 1, 8 and 15. Weights of the animals were taken on days 0, 7, 14, 22 and 24.

Figure 21:
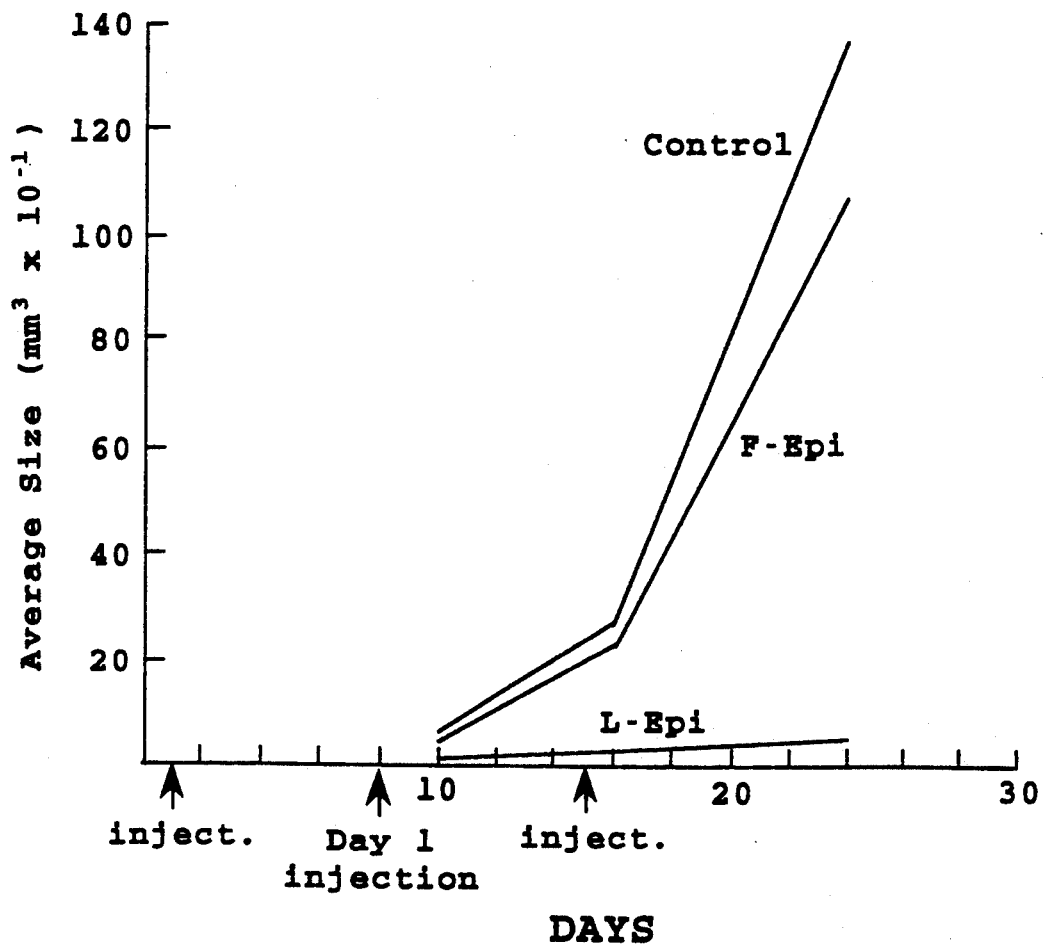
FIG. 21 is a plot showing growth kinetics of syngeneic mammary carcinoma (MC2) for three groups of 20 animals implanted bilaterally with $10^5$-$10^6$ tumor cells subcutaneously on day 0 and treated on days 1, 8 and 15 with saline control, or 6 mg/kg free epirubicin or PEG liposomes containing entrapped epirubicin, as indicated.

Results of the study are plotted in FIG. 21, where mean tumor size for the three treatment groups is as indicated, expressed as mean tumor size (in $mm^3 \times 10^{-1}$) for all three treatment groups. As shown, the tumor grows quickly in both the saline and free drug groups. In contrast, tumor growth is practically eliminated in the animals receiving the PEG liposomes with encapsulated epirubicin. At day 24 the statistical confidence between the liposome and free drug groups is extremely high (+ = 9.9, p < 0.0000001 using the Student's + tests).

From a clinical perspective, these animal data have important implications. In the U.S. and Western Europe, the highest mortality among cancer patients is in three tumor types: recurrent breast carcinoma, metastatic colo-rectal carcinoma and lung cancer. These solid tumors are refractory to current chemotherapeutic agents, even though cells excised from the tumors do respond when exposed directly to the drug in vitro. This dilemma has frustrated clinical oncologists for many years. The results from the treatment methods above show that the liposome delivery method of the present invention overcomes this in-vivo barrier to efficacy by selectively depositing drug at the tumor site, and thereby "restoring" the intrinsic activity of the drug.

EXAMPLE 16

Tumor Treatment Method

PEG-DOX liposomes were prepared as in Example 10 except that doxorubicin was loaded in the liposomes to a final level of 60–80 μg/μmoles total lipid. A doxorubicin HCl solution to be used as the free drug control was obtained from a hospital pharmacy. A total of 30 mice were injected IP with $10^6$, J-6456 lymphoma cells. The animals were divided into three 10-animal groups, each of which was injected IV with 0.4 ml of either saline vehicle, 10 mg/kg doxorubicin solution or the doxorubicin-loaded liposomes at 10 mg/kg. Each group was followed for 100 days for number of surviving animals. The percent survivors for each treatment group is plotted in FIG. 16.

As can be seen, free drug (filled circles) provided little improvement in survival over the saline group (filled squares). In the animals treated with doxorubicin loaded PEG-liposomes (filled triangles), however, about 50% of the animals survived over 40 days, 20% over 70 days, and 10% survived until the experiment was terminated at 100 days.

EXAMPLE 17

Reduced Toxicity of PEG-Liposomes

Solutions of free doxorubicin HCl, epirubicin HCl were obtained as above. PEG-liposome formulations containing either doxorubicin or epirubicin, at a drug concentration of 70–90 μg compound/μmole liposome lipid, were prepared as described in Example 10. Conventional liposomes (no PEG-derivatized lipid) were loaded with doxorubicin to a drug concentration of 40 μg/μmole lipid using standard techniques.

Each of the five formulations was administered to 35 mice, at a dose between 10 and 40 mg drug/kg body weight, in 5 mg/kg increments, with five receiving each dosage. The maximum tolerated dose given in Table 11 below is highest dose which did not cause death or dramatic weight loss in the injected animals within 14 days. As seen from the data, both DOX-liposomes and PEG-DOX liposomes more than doubled the tolerated dose of doxorubicin over the drug in free form, with the PEG-DOX liposomes giving a slightly higher tolerated dose. A similar result was obtained for doses of tolerated epirubicin in free and PEG-liposomal form.

TABLE 11

|  | Maximum Tolerated Dose of DXN (mg/Kg in mice) |
|---|---|
| DXN | 10–12 |
| DOX-Lip* | 25–30 |
| PEG-DXN-Lip | 25–35 |
| EPI | 10 |
| PEG-EPI-Lip | 20 |

*Conventional Doxorubicin Liposomes

Multidose toxicity studies were also conducted using doxo-rubicin and epirubicin in free form and encapsulated in PEG liposomes.

Table 12 below shows survival times of mice at 120 days following a single injection of free epirubicin and PEG liposomes with entrapped epirubicin, at drug doses between 3 and 15 mg/kg body weight, as indicated. 2/5 animals died at 9 mg/kg for free drug, versus the same mortality rate at 12 mg/kg for the liposome entrapped drug.

TABLE 12

| Dose | Surviving mice at 120 days | |
|---|---|---|
|  | Lip-Epi | Free-Epi |
| 3 mg/kg | 5/5 | 5/5 |
| 6 mg/kg | 5/5 | 5/5 |
| 9 mg/kg | 5/5 | 2/5 |
| 12 mg/kg | 2/5 | 0/5 |
| 15 mg/kg | 0/5 | 0/5 |

Figure 19:
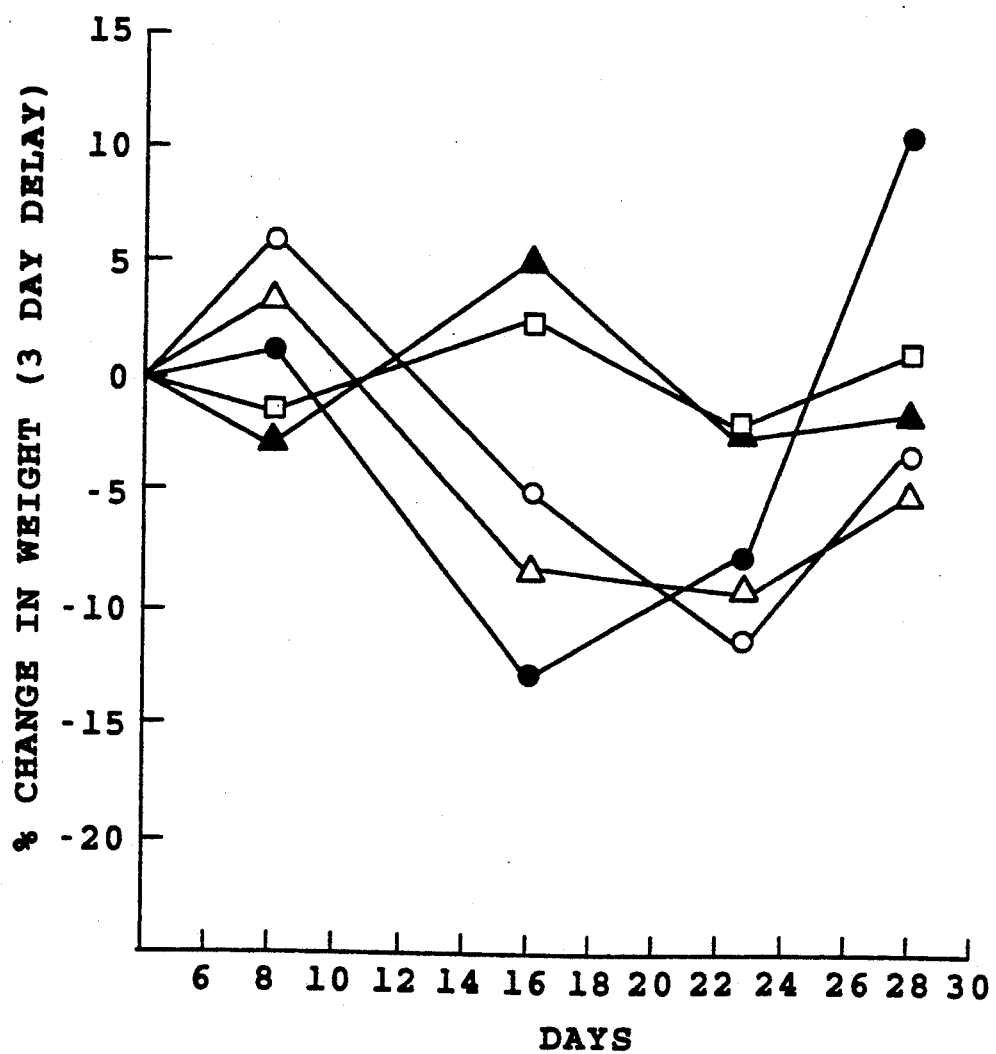
FIG. 19 is a plot showing the weight of animals expressed as percent change from pretreated levels for groups of seven mice which received on day 0, subcutaneous implantation of $10^6$ c-26 colon carcinoma cells, and which were injected intravenously on days 3, 10 and 17 with saline (closed circles), 6 mg/kg epirubicin (open circles), empty liposomes plug 6 mg/ky epirubicin (closed triangles), and PEG liposomes with entrapped epirubicin at 6 mg/kg (open triangles) or 9 mg/kg. (open squares)

The improved tolerance of animals to multiple doses of PEG-liposome-encapsulated epirubicin is seen in FIG. 19, which shows weight changes over a 26-day period following tumor implantation for five groups of 10 mice receiving either a saline control (closed circles), 6 mg/kg free epirubicin (open circles), 6 mg/kg free epirubicin plus empty liposomes (closed triangles), and PEG-liposomes containing epirubicin in entrapped form at doses of either 6 mg/kg (open triangles) or 9 mg/kg (open squares) in three weekly injections, starting on day 3 following tumor implantation. As shown, the animals in the saline, free epirubicin and free epirubicin/empty liposome groups lost weight rapidly starting about day 10, whereas the animals in both PEG-liposome-encapsulated epirubicin groups showed little weight loss throughout the study period.

Histological examination of heart muscle tissue in the above treatment groups showed no signs of cardiomyopathy in either of the liposome-entrapped drug group (6 or 9 mg/kg drug dose). By contrast, in both free drug groups (free drug alone and free drug plus empty liposomes), significant cardiomyopathy was observed.

Blood chemistries were measured in groups of both male and female mice receiving the same dose and injection schedule of free or PEG-liposomes with entrapped epirubicin as above. The results, presented in Table 13 below, show no significant changes from control values in the PEG liposome group with the exception of slightly elevated alkaline phosphatase levels.

TABLE 13

| Blood Biochemistry Results | | | | | | |
|---|---|---|---|---|---|---|
| | males | | | females | | |
| | Control | Free DOX | S-DOX | Control | Free DOX | S-DOX |
| Glucose (mmol/l) | 8 | 1.3 | 4.6 | 6.5 | 2.9 | 6.4 |
| Sodium (mmol/l) | 156 | 150 | 158 | 153 | 154 | 149 |
| Chloride (mmol/l) | 120 | 117 | 123 | 120 | 118 | 115 |
| Urea (mmol/l) | 8.1 | 12.4 | 8.8 | 7.3 | 12.5 | 6.7 |
| Creatinine ($\mu$mol/l) | 36 | 37 | 34 | 42 | 123 | 35 |
| Uric acid ($\mu$mol/l) | 138 | 333 | 151 | 97 | 350 | 108 |
| Total protein (g/l) | 53 | 39 | 54 | 56 | 57 | 53 |
| Albumin (g/l) | 31 | 21 | 32 | 34 | 31 | 32 |
| Bilirubin ($\mu$mol/l) | 0 | 0 | 0 | 0 | — | 1 |
| Cholesterol (mmol/l) | 2.7 | 6.0 | 3.1 | 2.3 | 4.7 | 2.1 |
| Alk. Phos. ($\mu$/l) | 155 | 129 | 21 | 143 | 162 | 215 |
| Calcium (mmol/l) | 2.4 | 1.6 | 2.6 | 2.6 | 2.9 | 2.4 |
| Phosphorus (mmol/l) | 3.9 | 5.2 | 3.6 | 3.9 | 3.4 | 3.2 |

Measurements made in a Technicon SMAC-1 analyzer using $\approx 1.5$ ml pooled serum from each experimental group.

Figure 20:
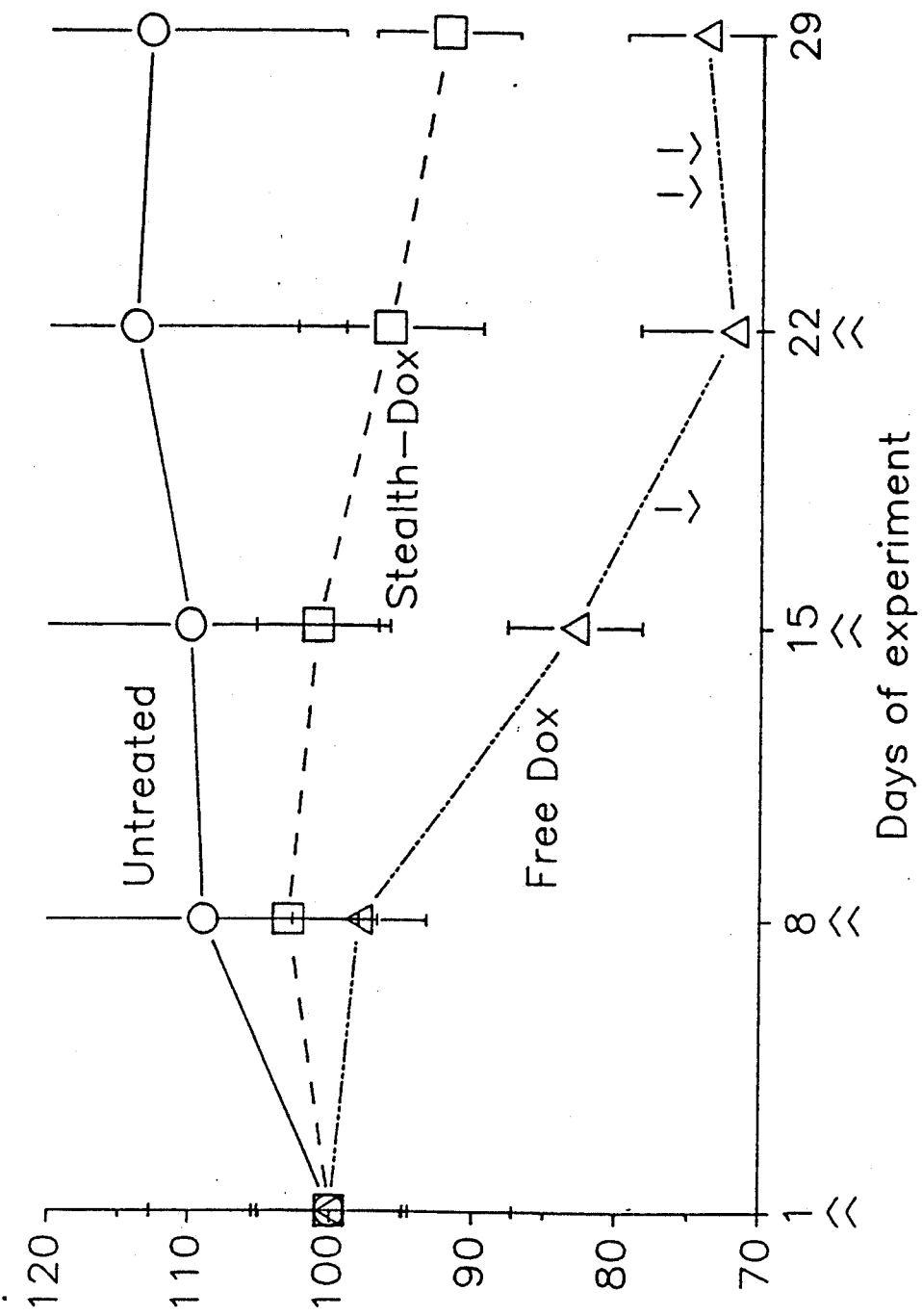
FIG. 20 is a plot of weight changes in normal Sabra male mice untreated (open circles) or treated with four weekly intravenous injections on days 1, 8, 5 and 22 with a 10 mg/kg dose of either free doxorubicin (open triangles) or PEG liposomes with entrapped doxorubicin (open squares)

Similar reduced toxicity results were obtained when free doxorubicin was compared with PEG liposomes with entrapped doxorubicin, in groups of mice receiving four weekly injections of 10 mg/kg doxorubicin on days 1, 8, 15 and 22. FIG. 20 shows weight changes for untreated mice (open circles) PEG liposomes with entrapped doxorubicin dox (open squares) and free doxorubicin (open triangles). Judged on the basis of weight loss in the trated animals, doxorubicin is clearly better tolerated when administered in the PEG liposome formulation. Comparative histopathological analysis in the animals, sacrificed on day 29 showed:

(a) In liver, hematopoiesis foci were present in both groups. In the free drug group, microcytosis was also observed. Otherwise, no hepatic damage was observed.

(b) In spleen, reversible atrophy of the red and white pulp was observed for both groups.

(c) In kidney, all free drug animals showed advanced signs of nephrosis. No damage was seen in the liposome group.

(d) In heart, mild to moderate myolysis was seen in all (13) mice receiving free drug. Mild damage was seen in only 2 of the (14) animals in the liposome group;

(e) In gonads, lack of follicular maturation and of spermatogenesis was seen in both groups.

(f) No damage was observed in lungs, adrenals, small bowel, pancreas, or urinary bladder in either group.

In summary, PEG-liposomes effectively protected the animals against doxorubicin damage to kidneys and heart. No significant difference was seen in the damage to the hematopoietic system (spleen).

EXAMPLE 18

Failure of Tumor Treatment with Liposomes Conventional Doxorubicin

Conventional doxorubicin liposomes (L-DOX) were prepared according to published methods (Gabizon, 1988). Briefly, a mixture of eggPG, Egg,PC, cholesterol and a-TC in a mole ratio of 0.3: 1.4: 1: 0.2 was made in chloroform. The solvent was removed under reduced pressure and the dry lipid film hydrated with a solution of 155 mM NaCl containing 2-5 mg doxorubicin HCl. The resulting MLV preparation was down-sized by extrusion through a series of polycarbonate membranes to a final size of about 250 nm. The free (unentrapped) drug was removed by passing the suspension over a bed of Dowex resin. The final doxorubicin concentration was about 40 per $\mu$mole lipid.

Three groups of 7 mice were inoculated subcutaneously with $10^5$–$10^6$ C-26 colon carcinoma cells as detailed in Example 15. The animals were divided into three, 7-animal treatment groups, one of which received 0.5 ml of saline vehicle as a control. The other two groups were treated with doxorubicin either as a free drug solution or in the form of L-DOX liposomes at a dose of 10 mg/kg. The treatments were given on days 8, 15 and 22 after tumor cell inoculation. Tumor size was measured on the days treatments were given and day 28. As shown in FIG. 17, the free drug (filled circles) suppressed tumor growth to a modest extent compared with the saline control (solid line). The tumor in the L-Dox-treated group (filled triangles) grew slightly faster than the free-drug-treated group and slightly more slowly than in the untreated group. These results indicate that the anti-tumor activity of the L-DOX preparation is about the same, and certainly no better than the same dose of free drug. This stands in marked contrast to the results presented in Example 15 (and FIGS. 15A-C) which show that at comparable doses epirubicin entrapped in PEG-liposomes has dramatically better anti-tumor activity than free drug in this same tumor model.

Although the invention has been described and illustrated with respect to particular derivatized lipid compounds, liposome compositions, and use, it will be apparent that a variety of modifications and changes may be made without departing from the invention.

It is claimed:

1. A liposome composition for use in localizing a compound in a solid tumor via the bloodstream, by liposome extravasation into the tumor, comprising liposomes (i) composed of vesicle-forming lipids and between 1-20 mole percent of an amphipathic vesicle-forming lipid derivatized with a hydrophilic polymer selected from the group consisting of polyethyleneglycol, polylactic acid, polyglycolic acid and polylactic acid/polyglycolic acid copolymers, and (ii) having a selected mean particle diameter in the size range between about 0.07 to 0.12 microns, and the compound in liposome-entrapped form, and characterized by a liposome blood lifetime, 24 hours after intravenous injection, that is several times greater than the blood lifetime of liposomes in the absence of the derivatized lipid.

2. The composition of claim 1, wherein the hydrophilic polymer is polyethyleneglycol having a molecular weight between about 1,000–5,000 daltons.

3. The composition of claim 2, wherein the hydrophilic polymer is selected from the group of polylactic acid, polyglycolic acid, and copolymers thereof.

4. The composition of claim 1, wherein the compound is an anti-tumor agent, and at least about 80% of the compound is in liposome-entrapped form.

5. The composition of claim 4, wherein the anti-tumor agent is an anthracycline antibiotic, and the concentration of compound which is entrapped in the liposomes is greater than 50 µg compound/µmole liposome lipid.

6. The composition of claim 4, wherein the anthracycline is selected from the group consisting of doxorubicin, epirubicin, and daunorubicin, including pharmacologically acceptable salts and acids thereof.

7. A liposome composition for use in localizing an anthracycline anti-tumor drug in a solid tumor via the bloodstream by liposome extravasation into the tumor, comprising, liposomes (i) composed of vesicle-forming lipids and between 1–20 mole percent of an amphipathic vesicle-forming lipid derivatized with polyethyleneglycol, and (ii) having an average size in a selected size range between about 0.07 to 0.12 microns, and the drug, at least about 80% in liposome-entrapped form, and having a concentration in the liposomes greater than 50 µg agent/µmole liposome lipid, and characterized by a liposome blood lifetime, 24 hours after intravenous injection, that is several times greater than the blood lifetime of liposomes in the absence of the derivatized lipid.

8. A method of preparing an agent for localization in a solid tumor by extravasation of liposomes containing the agent into the solid tumor, when the agent is administered by IV injection, comprising entrapping the agent in liposomes which are characterized by:

(a) a lipid composition which includes between 1–20 mole percent of an amphipathic vesicle-forming lipid derivatized with a hydrophilicpolymer selected from the group consisting of polyethyleneglycol, polylactic acid, polyglycolic acid and polyactic acid/polyglycolic acid copolymers, (b) an average liposome size in a selected size range between about 0.07–0.12 microns; and (c) a liposome blood lifetime 24 hours after intravenous injection, that is several times greater than the blood lifetime of liposomes in the absence of the derivatized lipid.

9. The method of claim 8, wherein the agent is an anthracycline antibiotic drug, and said entrapping includes loading the agent into preformed liposomes by remote loading across an ion or pH gradient, to a final concentration of lipisome-entrapped material of greater than about 50 µg agent/µmole liposome lipid.

10. The method of claim 9, wherein the drug is selected from the group consisting of doxorubicin, epirubicin, and daunorubicin, including pharmacologically acceptable salts and acids thereof.

11. A method of localizing a compound in a solid tumor in a subject by extravasation of liposomes containing the agent into the solid tumor comprising, preparing a composition of liposomes (i) composed of vesicle-forming lipids and between 1–20 mole percent of an amphipathic vesicle-forming lipid derivatized with a hydrophilic polymer selected from the group consisting of polyethyleneglycol, polylactic acid, polyglycolic acid and polylactic acid/polyglycolic acid copolymers, said liposomes having a blood lifetime, as measured by the percent of a liposome marker present in the blood 24 hours after intravenous administration, which is several times greater than that of liposomes in absence of the derivatized lipids, (ii) having an average size in a selected size range between about 0.07–0.12 microns, and (iii) containing the compound in liposome-entrapped form, injecting the composition intravenously in the subject in an amount effective to localize a therapeutically effective quantity of the agent in the solid tumor, and by said injecting, achieving a localization of the liposomes in the solid tumor, 48 hours after intravenous administration, that is substantially greater than that of liposomes in the absence of the derivatized lipid.

12. The method of claim 11, wherein the hydrophilic polymer is polyethyleneglycol having a molecular weight between about 1,000–5,000 daltons.

13. A method of treating breast or colon carcinoma in a subject with an anthracycline antibiotic drug, comprising entrapping the drug in liposomes (i) composed of vesicle-forming lipids and between 1–20 mole percent of an amphipathic vesicle-forming lipid derivatized with a hydrophilic polymer selected from the group consisting of polyethyleneglycol, polylactic acid, polyglycolic acid and polylactic acid/polyglycolic acid copolymers, said liposomes having a blood lifetime, as measured by the percent of a liposome marker present in the blood 24 hours after intravenous administration, which is several times greater than that of liposomes in absence of the derivatized lipids, and (ii) having an average size in a selected size range between about 0.07–0.12 microns at a concentration of entrapped drug of greater than about 50 µg drug/µmole liposome lipid, with at least about 80% of the drug entrapped in the liposomes, and injecting the composition intravenously in the subject in an amount effective to localize a therapeutically effective quantity of the agent in the carcinoma.

14. The method of claim 13, wherein the hydrophilic polymer is polyethyleneglycol having a molecular weight between about 1,000–5,000 daltons, and the agent is selected from the group consisting of doxorubicin, epirubicin, and daunorubicin, including a pharmacologically acceptable salts and acids thereof.

15. The composition of claim 7, wherein the drug is selected from the group consisting of doxorubicin, epirubicin, and daunorubicin, including pharmacologically acceptable salts and acids thereof.

* * * * *

UNITED STATES PATENT AND TRADEMARK OFFICE
CERTIFICATE OF CORRECTION

PATENT NO. : 5,213,804

DATED : May 25, 1993

INVENTOR(S) : F. J. Martin, et al

It is certified that error appears in the above-indentified patent and that said Letters Patent is hereby corrected as shown below:

On the title page : Item [*] Notice: should read -- The portion of the term of this patent subsequent to October 20, 2009 has been disclaimed. --

Signed and Sealed this

Ninth Day of April, 1996

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

| | | |
|---|---|---|
| PATENT NO. | : 5,213,804 | Page 1 of 1 |
| APPLICATION NO. | : 07/642321 | |
| DATED | : May 25, 1993 | |
| INVENTOR(S) | : Francis J. Martin et al. | |

It is certified that error appears in the above-identified patent and that said Letters Patent is hereby corrected as shown below:

Column 5:
On line 37, replace "PEG-liposomal" with --HPI-liposomal--.

Column 16:
On line 21, replace "PEG-liposomes" with --HPI-liposomes--; on line 30, replace "PEG-liposomes" with --HPI-liposomes--; on line 50, delete "shown in Table 9"; and on line 63, replace "liposome-associated" with --HPI-liposome-associated--.

Column 34
On line 24, before "PEG-liposomes" insert --HPI-liposomal and--; on line 25, replace "Example 10" with --Example 11-- and after "PEG-DOX" insert --and HPI DOX--; on line 33, replace "PEG" with --HPI--; on line 48, replace "PEG-liposomes" with --HPI-liposomes--; and on line 57, replace "PEG" with --HPI--.

Column 35:
On line 11, replace "llymphoma" with --lymphoma--.

Signed and Sealed this

Fifth Day of December, 2006

JON W. DUDAS
*Director of the United States Patent and Trademark Office*